(12) United States Patent
DiPerna

(10) Patent No.: US 8,986,253 B2
(45) Date of Patent: Mar. 24, 2015

(54) TWO CHAMBER PUMPS AND RELATED METHODS

(75) Inventor: Paul M. DiPerna, San Clemente, CA (US)

(73) Assignee: Tandem Diabetes Care, Inc., San Diego, CA (US)

(*) Notice: Subject to any disclaimer, the term of this patent is extended or adjusted under 35 U.S.C. 154(b) by 910 days.

(21) Appl. No.: 12/538,018

(22) Filed: Aug. 7, 2009

(65) Prior Publication Data

US 2010/0008795 A1 Jan. 14, 2010

Related U.S. Application Data

(63) Continuation-in-part of application No. 12/020,498, filed on Jan. 25, 2008, now abandoned.

(51) Int. Cl.
| | |
|---|---|
| *A61M 37/00* | (2006.01) |
| *F04B 43/00* | (2006.01) |
| *F04B 45/02* | (2006.01) |
| *A61M 5/148* | (2006.01) |
| *A61M 5/168* | (2006.01) |
| *F04B 43/06* | (2006.01) |
| *F04B 43/10* | (2006.01) |

(52) U.S. Cl.
CPC ......... *A61M 5/1486* (2013.01); *A61M 5/16809* (2013.01); *A61M 5/16886* (2013.01); *F04B 43/06* (2013.01); *F04B 43/10* (2013.01); *A61M 2205/3331* (2013.01); *A61M 2205/3368* (2013.01)
USPC .............................. 604/141; 604/132; 417/473

(58) Field of Classification Search
CPC ...................... A61M 5/14586; A61M 5/14593; A61M 5/148; A61M 5/1483; A61M 5/1486; A61M 5/152; A61M 5/155; A61M 5/16809
USPC .............. 417/53, 54, 472, 473; 604/131, 132, 604/140, 141
See application file for complete search history.

(56) References Cited

U.S. PATENT DOCUMENTS

| | | |
|---|---|---|
| 318,856 A | 5/1885 | Bilz |
| 329,881 A | 11/1885 | Benton |
| 332,402 A | 12/1885 | Leadley |
| 596,062 A | 12/1897 | Firey |
| 722,431 A | 3/1903 | Packard |
| 818,938 A | 4/1906 | Crane |

(Continued)

FOREIGN PATENT DOCUMENTS

| | | |
|---|---|---|
| CN | 1229347 A | 9/1999 |
| CN | 2668155 Y | 1/2005 |

(Continued)

OTHER PUBLICATIONS

U.S. Appl. No. 60/789,243, filed Apr. 5, 2006, Beavis.

(Continued)

*Primary Examiner* — Peter J Bertheaud
(74) *Attorney, Agent, or Firm* — Patterson Thuente Pedersen, P.A.

(57) ABSTRACT

Two chamber pumps and related methods provide a platform for measuring flow rate in about real time without contacting the material being pumped. Pressure and optional temperature sensors disposed in a pressurized chamber allow for flow material delivery calculations after being calibrated or by knowing the initial volume of the flow material to be delivered.

21 Claims, 3 Drawing Sheets

(56) References Cited

U.S. PATENT DOCUMENTS

| | | |
|---|---|---|
| 926,092 A | 6/1909 | Bright |
| 1,079,522 A | 11/1913 | Smith |
| 1,274,884 A | 8/1918 | Hudson |
| 1,304,036 A | 5/1919 | Eshelby |
| 1,314,987 A | 9/1919 | Smith |
| 1,643,021 A | 9/1927 | Luyties |
| 1,657,663 A | 6/1928 | Devereux |
| 1,866,061 A | 7/1932 | Schoel |
| 1,910,032 A | 5/1933 | Mills |
| 2,018,316 A | 10/1935 | Ownings |
| 2,029,630 A | 2/1936 | McMichael |
| 2,147,164 A | 2/1939 | Kent |
| 2,398,234 A | 4/1946 | Long |
| 2,412,397 A | 12/1946 | Harper |
| 2,444,677 A | 7/1948 | Rosenblum |
| 2,454,929 A | 11/1948 | Kempton |
| 2,495,693 A | 1/1950 | Byrd, Jr. et al. |
| 2,497,020 A | 2/1950 | Singer |
| 2,568,519 A | 9/1951 | Smith |
| 2,599,325 A | 6/1952 | Fritzberg |
| 2,629,402 A | 2/1953 | Cook |
| 2,667,900 A | 2/1954 | Cantalupo |
| 2,674,262 A | 4/1954 | Bradshaw |
| 2,679,954 A | 6/1954 | Barnes |
| 2,701,583 A | 2/1955 | Rux |
| 2,706,612 A | 4/1955 | Ratelband |
| 2,728,355 A | 12/1955 | Dahl |
| 2,735,642 A | 2/1956 | Norman |
| 2,736,463 A | 2/1956 | Michael |
| 2,746,709 A | 5/1956 | Minor |
| 2,764,183 A | 9/1956 | Gollehon |
| 2,781,058 A | 2/1957 | Warhus |
| 2,834,379 A | 5/1958 | Fields |
| 2,841,237 A | 7/1958 | Slayter |
| 2,852,033 A | 9/1958 | Orser |
| 2,878,836 A | 3/1959 | Binks |
| 2,891,578 A | 6/1959 | Dahl et al. |
| 2,898,078 A | 8/1959 | Stephenson et al. |
| 2,898,088 A | 8/1959 | Alder |
| 2,899,979 A | 8/1959 | Dahl et al. |
| 2,936,788 A | 5/1960 | Dahl et al. |
| 2,939,487 A | 6/1960 | Fraser et al. |
| 2,960,109 A | 11/1960 | Wilson |
| 2,968,318 A | 1/1961 | Bauman |
| 2,971,466 A | 2/1961 | Corbett |
| 2,989,086 A | 6/1961 | Dahl |
| 3,017,903 A | 1/1962 | Steffens |
| 3,023,750 A * | 3/1962 | Baron .......................... 604/141 |
| 3,035,613 A | 5/1962 | Beatty |
| 3,060,966 A | 10/1962 | Ratelband |
| 3,061,039 A | 10/1962 | Peters |
| 3,070,132 A | 12/1962 | Sheridan |
| 3,072,151 A | 1/1963 | Quercia |
| 3,077,903 A | 2/1963 | Honsinger |
| 3,095,120 A | 6/1963 | Steiner et al. |
| 3,095,175 A | 6/1963 | Iketani |
| 3,118,646 A | 1/1964 | Markey |
| 3,121,445 A | 2/1964 | Wisniewski |
| 3,123,900 A | 3/1964 | Millar |
| 3,133,678 A | 5/1964 | Marwell et al. |
| 3,143,861 A | 8/1964 | Dumas |
| 3,153,414 A * | 10/1964 | Beall et al. ...................... 222/95 |
| 3,174,694 A | 3/1965 | Kitabayshi |
| 3,187,562 A | 6/1965 | Rolfson |
| 3,189,125 A | 6/1965 | Windsor et al. |
| 3,195,586 A | 7/1965 | Vogt |
| 3,202,178 A | 8/1965 | Milton |
| 3,203,662 A | 8/1965 | Lau |
| 3,214,903 A | 11/1965 | Cochran |
| 3,216,451 A | 11/1965 | Smallpeice |
| 3,227,311 A | 1/1966 | Rowell |
| 3,298,394 A | 1/1967 | Chorkey |
| 3,302,578 A | 2/1967 | Anderson |
| 3,318,138 A | 5/1967 | Rolfson |
| 3,338,049 A | 8/1967 | Fernberger |
| 3,347,418 A | 10/1967 | Fefferman |
| 3,376,625 A | 4/1968 | McCulloch |
| 3,409,050 A | 11/1968 | Weese |
| 3,428,223 A | 2/1969 | Lewiecki et al. |
| 3,430,659 A | 3/1969 | Henderson |
| 3,455,147 A | 7/1969 | Peck et al. |
| 3,479,002 A | 11/1969 | Hirs |
| 3,493,496 A | 2/1970 | Bray et al. |
| 3,508,587 A | 4/1970 | Mauch |
| 3,532,125 A | 10/1970 | Everett et al. |
| 3,556,159 A | 1/1971 | Bleasdale |
| 3,568,847 A | 3/1971 | Carr |
| 3,583,603 A | 6/1971 | Freckmann et al. |
| 3,586,040 A | 6/1971 | Urback |
| 3,596,939 A | 8/1971 | Gibson |
| 3,620,500 A | 11/1971 | Santomieri |
| 3,621,882 A | 11/1971 | Kupiec |
| 3,648,694 A | 3/1972 | Mogos et al. |
| 3,654,959 A | 4/1972 | Kassel |
| 3,665,967 A | 5/1972 | Kachnik |
| 3,673,853 A | 7/1972 | Griswold et al. |
| 3,674,183 A | 7/1972 | Venable et al. |
| 3,675,672 A | 7/1972 | Freeman |
| 3,693,484 A | 9/1972 | Sanderson, Jr. |
| 3,696,958 A | 10/1972 | Lee |
| 3,699,812 A | 10/1972 | Masnik |
| 3,717,174 A | 2/1973 | Dewall |
| 3,724,234 A | 4/1973 | Garavelli |
| 3,756,459 A | 9/1973 | Bannister et al. |
| 3,833,019 A | 9/1974 | Diggs |
| 3,836,113 A | 9/1974 | Johnson |
| 3,837,363 A | 9/1974 | Meronek |
| 3,838,794 A * | 10/1974 | Cogley et al. .................. 604/141 |
| 3,847,178 A | 11/1974 | Keppel |
| 3,860,353 A | 1/1975 | Lukasik et al. |
| 3,894,538 A | 7/1975 | Richter |
| 3,899,135 A | 8/1975 | O'Brian |
| 3,918,674 A | 11/1975 | Sutter |
| 3,946,761 A | 3/1976 | Thompson et al. |
| RE28,890 E | 7/1976 | Ingram et al. |
| 3,970,105 A | 7/1976 | Pelton et al. |
| 3,985,133 A | 10/1976 | Jenkins et al. |
| 3,991,972 A | 11/1976 | Eaton |
| 4,000,857 A | 1/1977 | Moen |
| 4,003,398 A | 1/1977 | Duveau |
| 4,023,772 A | 5/1977 | Ratelband |
| 4,028,931 A | 6/1977 | Bisera et al. |
| 4,032,265 A | 6/1977 | Miller |
| 4,076,872 A | 2/1978 | Lewicki et al. |
| 4,087,301 A | 5/1978 | Steadman |
| 4,089,206 A | 5/1978 | Raffel et al. |
| 4,103,689 A | 8/1978 | Leighton |
| 4,105,050 A | 8/1978 | Hendrickson et al. |
| 4,106,510 A | 8/1978 | Hakim et al. |
| 4,111,391 A | 9/1978 | Pilolla |
| 4,137,913 A | 2/1979 | Georgi |
| 4,156,127 A | 5/1979 | Sako et al. |
| 4,178,938 A | 12/1979 | Au |
| 4,191,184 A | 3/1980 | Carlisle |
| 4,191,204 A | 3/1980 | Nehring |
| 4,191,358 A | 3/1980 | Ferri |
| 4,193,552 A | 3/1980 | Ishikawa |
| 4,195,810 A | 4/1980 | Lavin |
| 4,215,726 A | 8/1980 | Tagami |
| 4,228,956 A | 10/1980 | Varner |
| 4,248,270 A | 2/1981 | Ostrowski |
| 4,250,872 A | 2/1981 | Tamari |
| 4,254,791 A | 3/1981 | Bron |
| 4,265,241 A | 5/1981 | Portner et al. |
| 4,271,989 A | 6/1981 | O'Neill |
| 4,275,727 A | 6/1981 | Keeri-Szanto |
| 4,314,621 A | 2/1982 | Hansen |
| 4,314,979 A | 2/1982 | Deabriges |
| 4,327,845 A | 5/1982 | Keyes et al. |
| 4,330,071 A | 5/1982 | Ohlson |
| 4,344,459 A | 8/1982 | Nelson |
| 4,356,935 A | 11/1982 | Kamin |
| 4,367,786 A | 1/1983 | Hafner et al. |
| 4,382,453 A | 5/1983 | Bujan et al. |

(56) References Cited

U.S. PATENT DOCUMENTS

| | | |
|---|---|---|
| 4,405,294 A | 9/1983 | Albarda |
| 4,406,656 A | 9/1983 | Hattler et al. |
| 4,416,596 A | 11/1983 | Lichtenstein |
| 4,432,468 A | 2/1984 | Siff et al. |
| 4,440,154 A | 4/1984 | Bellows |
| 4,440,323 A | 4/1984 | Benson |
| 4,443,218 A | 4/1984 | DeCant et al. |
| 4,448,538 A | 5/1984 | Mantel |
| 4,457,343 A | 7/1984 | Zukausky |
| 4,469,481 A | 9/1984 | Kobayashi |
| 4,481,808 A | 11/1984 | Sakata et al. |
| 4,492,339 A | 1/1985 | Kreitzberg |
| 4,498,843 A | 2/1985 | Schneider et al. |
| 4,508,144 A | 4/1985 | Bernett |
| 4,515,536 A | 5/1985 | van Os |
| 4,520,948 A | 6/1985 | Hampel et al. |
| 4,527,595 A | 7/1985 | Jorgensen et al. |
| 4,529,106 A | 7/1985 | Broadfoot et al. |
| 4,529,401 A | 7/1985 | Leslie et al. |
| 4,538,616 A | 9/1985 | Rogoff |
| 4,557,726 A | 12/1985 | Reinicke |
| 4,559,036 A | 12/1985 | Wunsch |
| 4,562,960 A | 1/1986 | Marty et al. |
| 4,570,745 A | 2/1986 | Sparks et al. |
| 4,592,390 A | 6/1986 | Boyd |
| 4,609,014 A | 9/1986 | Jurevic et al. |
| 4,620,648 A | 11/1986 | Schwartzman |
| 4,624,661 A | 11/1986 | Airmond |
| 4,627,573 A | 12/1986 | Havens et al. |
| 4,628,928 A | 12/1986 | Lowell |
| 4,636,226 A | 1/1987 | Canfora |
| 4,646,945 A | 3/1987 | Steiner et al. |
| 4,649,959 A | 3/1987 | Wadleigh |
| 4,650,471 A | 3/1987 | Tamari |
| 4,651,781 A | 3/1987 | Kandelman |
| 4,657,486 A | 4/1987 | Stempfle et al. |
| 4,666,430 A | 5/1987 | Brown et al. |
| 4,667,700 A | 5/1987 | Buzzi |
| 4,673,415 A | 6/1987 | Stanford |
| 4,684,364 A | 8/1987 | Sawyer et al. |
| 4,684,367 A | 8/1987 | Schaffer et al. |
| 4,687,423 A | 8/1987 | Maget |
| 4,713,063 A | 12/1987 | Krumme |
| 4,718,893 A | 1/1988 | Dorman et al. |
| 4,724,870 A | 2/1988 | Mølbæk et al. |
| 4,741,736 A | 5/1988 | Brown |
| 4,770,211 A | 9/1988 | Olsson |
| 4,773,448 A | 9/1988 | Francis |
| 4,776,842 A | 10/1988 | Franetzki et al. |
| 4,778,451 A | 10/1988 | Kamen |
| 4,779,762 A | 10/1988 | Klein et al. |
| 4,787,408 A | 11/1988 | Twerdochlib |
| 4,808,167 A | 2/1989 | Mann et al. |
| 4,810,243 A | 3/1989 | Howson |
| 4,823,844 A | 4/1989 | Bartholomew |
| 4,826,482 A | 5/1989 | Kamen |
| 4,840,191 A | 6/1989 | Gausman et al. |
| 4,869,431 A | 9/1989 | Jubert et al. |
| 4,871,093 A | 10/1989 | Burshtain et al. |
| 4,878,896 A | 11/1989 | Garrison et al. |
| 4,883,093 A | 11/1989 | Miles et al. |
| 4,886,499 A | 12/1989 | Cirelli et al. |
| 4,886,514 A | 12/1989 | Maget |
| 4,893,966 A | 1/1990 | Rohel |
| 4,897,906 A | 2/1990 | Bartholomew |
| 4,902,278 A | 2/1990 | Maget |
| 4,908,017 A | 3/1990 | Howson et al. |
| 4,931,050 A | 6/1990 | Idriss |
| 4,938,259 A | 7/1990 | Schmidt |
| 4,955,860 A | 9/1990 | Ruano |
| 4,969,884 A | 11/1990 | Yum |
| 4,973,402 A | 11/1990 | Johnson et al. |
| 4,976,162 A | 12/1990 | Kamen |
| 4,985,015 A | 1/1991 | Oberman et al. |
| 4,986,312 A | 1/1991 | Gute |
| 4,989,456 A | 2/1991 | Stupecky |
| 4,995,258 A | 2/1991 | Frank |
| 5,000,739 A | 3/1991 | Kulisz et al. |
| 5,002,527 A | 3/1991 | Reller et al. |
| 5,005,403 A | 4/1991 | Steudle et al. |
| 5,006,997 A | 4/1991 | Reich |
| 5,011,477 A | 4/1991 | Winchell et al. |
| 5,027,861 A | 7/1991 | Gute |
| 5,035,865 A | 7/1991 | Inaba et al. |
| 5,038,821 A | 8/1991 | Maget |
| 5,044,900 A | 9/1991 | Cavallaro |
| 5,047,044 A | 9/1991 | Smith et al. |
| 5,049,141 A | 9/1991 | Olive |
| 5,050,612 A | 9/1991 | Matsumura |
| 5,053,001 A | 10/1991 | Reller et al. |
| 5,053,189 A | 10/1991 | Chrise et al. |
| 5,059,182 A | 10/1991 | Laing |
| 5,062,834 A | 11/1991 | Gross et al. |
| 5,062,841 A | 11/1991 | Siegel |
| 5,076,911 A | 12/1991 | Brown et al. |
| 5,078,683 A | 1/1992 | Sancoff et al. |
| 5,082,240 A | 1/1992 | Richmond |
| 5,082,503 A | 1/1992 | Sluga et al. |
| 5,083,908 A | 1/1992 | Gagnebin et al. |
| 5,084,021 A | 1/1992 | Baldwin |
| 5,085,644 A | 2/1992 | Watson et al. |
| 5,087,245 A | 2/1992 | Daon |
| 5,090,963 A | 2/1992 | Gross et al. |
| 5,091,091 A | 2/1992 | Terman |
| 5,091,094 A | 2/1992 | Veech |
| 5,103,211 A | 4/1992 | Daoud et al. |
| 5,104,526 A | 4/1992 | Brown et al. |
| 5,108,363 A | 4/1992 | Tuttle et al. |
| 5,125,781 A | 6/1992 | Breunig et al. |
| 5,126,324 A | 6/1992 | Clark et al. |
| 5,127,258 A | 7/1992 | Brown et al. |
| 5,128,145 A | 7/1992 | Edgren et al. |
| 5,131,816 A | 7/1992 | Brown et al. |
| 5,135,491 A | 8/1992 | Baldwin |
| 5,135,498 A | 8/1992 | Kam et al. |
| 5,135,499 A | 8/1992 | Tafani et al. |
| 5,149,413 A | 9/1992 | Maget |
| 5,154,712 A | 10/1992 | Herweck et al. |
| 5,156,591 A | 10/1992 | Gross et al. |
| 5,156,598 A | 10/1992 | Skakoon et al. |
| 5,157,960 A | 10/1992 | Brehm et al. |
| 5,158,230 A | 10/1992 | Curran |
| 5,170,912 A | 12/1992 | Du |
| 5,173,302 A | 12/1992 | Holmblad et al. |
| 5,176,502 A | 1/1993 | Sanderson et al. |
| 5,178,603 A | 1/1993 | Prince |
| 5,182,258 A | 1/1993 | Chiou |
| 5,184,359 A | 2/1993 | Tsukamura et al. |
| 5,186,431 A | 2/1993 | Tamari |
| 5,186,805 A | 2/1993 | Gross et al. |
| 5,188,258 A | 2/1993 | Iwashita |
| 5,190,522 A | 3/1993 | Wojcicki et al. |
| 5,191,719 A | 3/1993 | Kitt |
| 5,192,264 A | 3/1993 | Fossel |
| 5,192,272 A * | 3/1993 | Faure ............................ 604/141 |
| 5,203,506 A | 4/1993 | Gross et al. |
| 5,207,642 A | 5/1993 | Orkin et al. |
| 5,207,645 A | 5/1993 | Ross et al. |
| 5,207,666 A | 5/1993 | Idriss et al. |
| 5,209,265 A | 5/1993 | Taguri et al. |
| 5,215,450 A | 6/1993 | Tamari |
| 5,217,440 A | 6/1993 | Frassica |
| 5,218,987 A | 6/1993 | Heil |
| 5,220,515 A | 6/1993 | Freerks et al. |
| 5,224,796 A | 7/1993 | Zeman |
| 5,226,446 A | 7/1993 | Cooper |
| 5,228,291 A | 7/1993 | Meyering |
| 5,228,842 A | 7/1993 | Guebeli et al. |
| 5,232,437 A | 8/1993 | Lysaght et al. |
| 5,232,449 A | 8/1993 | Stern et al. |
| 5,240,603 A | 8/1993 | Frank et al. |
| 5,241,935 A | 9/1993 | Beck et al. |
| 5,242,406 A | 9/1993 | Gross et al. |
| 5,242,408 A | 9/1993 | Jhuboo et al. |

(56) References Cited

U.S. PATENT DOCUMENTS

| | | |
|---|---|---|
| 5,243,983 A | 9/1993 | Tarr et al. |
| 5,246,147 A | 9/1993 | Gross |
| 5,247,434 A | 9/1993 | Peterson et al. |
| 5,254,096 A | 10/1993 | Rondelet et al. |
| 5,256,157 A | 10/1993 | Samiotes et al. |
| 5,257,971 A | 11/1993 | Lord et al. |
| 5,259,399 A | 11/1993 | Brown |
| 5,259,732 A | 11/1993 | Stern |
| 5,261,459 A | 11/1993 | Atkinson et al. |
| 5,261,884 A | 11/1993 | Stern et al. |
| 5,266,265 A | 11/1993 | Raible |
| 5,270,005 A | 12/1993 | Raible |
| 5,271,724 A | 12/1993 | vanLintel |
| 5,272,294 A | 12/1993 | Charboneau et al. |
| 5,272,909 A | 12/1993 | Nguyen et al. |
| 5,273,406 A | 12/1993 | Feygin |
| 5,273,518 A | 12/1993 | Lee et al. |
| 5,278,142 A | 1/1994 | Chiou |
| 5,279,543 A | 1/1994 | Glikfeld et al. |
| 5,279,586 A | 1/1994 | Balkwell |
| 5,290,684 A | 3/1994 | Kelly |
| 5,295,966 A | 3/1994 | Stern et al. |
| 5,295,967 A | 3/1994 | Rondelet et al. |
| 5,295,976 A | 3/1994 | Harris |
| 5,303,843 A | 4/1994 | Zink et al. |
| 5,304,126 A | 4/1994 | Epstein et al. |
| 5,304,163 A | 4/1994 | Bonnici et al. |
| 5,312,233 A | 5/1994 | Tanny et al. |
| 5,320,250 A | 6/1994 | La et al. |
| 5,321,392 A | 6/1994 | Skakoon et al. |
| 5,322,418 A | 6/1994 | Comer |
| 5,322,620 A | 6/1994 | Brown et al. |
| 5,322,626 A | 6/1994 | Frank et al. |
| 5,327,777 A | 7/1994 | Kaye et al. |
| 5,334,162 A | 8/1994 | Harris |
| 5,335,705 A | 8/1994 | Morishita et al. |
| 5,335,852 A | 8/1994 | Muntean et al. |
| 5,336,051 A | 8/1994 | Tamari |
| 5,338,157 A | 8/1994 | Blomquist |
| 5,339,865 A | 8/1994 | Asghar et al. |
| 5,341,783 A | 8/1994 | Beck et al. |
| 5,345,488 A | 9/1994 | Skipper et al. |
| 5,348,197 A | 9/1994 | Mizzi et al. |
| 5,349,933 A | 9/1994 | Hasegawa et al. |
| 5,350,224 A | 9/1994 | Nell et al. |
| 5,352,201 A | 10/1994 | Jemmott |
| 5,354,273 A | 10/1994 | Hagen |
| 5,356,375 A | 10/1994 | Higley et al. |
| 5,356,378 A | 10/1994 | Doan |
| 5,356,632 A | 10/1994 | Gross et al. |
| 5,358,635 A | 10/1994 | Frank et al. |
| 5,360,062 A | 11/1994 | White |
| 5,360,734 A | 11/1994 | Chapman et al. |
| 5,362,307 A | 11/1994 | Guy et al. |
| 5,364,242 A | 11/1994 | Olsen |
| 5,366,904 A | 11/1994 | Quereshi et al. |
| 5,367,910 A | 11/1994 | Woodward |
| 5,368,555 A | 11/1994 | Sussman et al. |
| 5,369,976 A | 12/1994 | Ratton |
| 5,370,622 A | 12/1994 | Livingston et al. |
| 5,370,870 A | 12/1994 | Wong |
| 5,373,865 A | 12/1994 | Jung et al. |
| 5,381,823 A | 1/1995 | DiBartolo |
| 5,384,709 A | 1/1995 | Seder et al. |
| 5,387,327 A | 2/1995 | Khan |
| 5,388,453 A | 2/1995 | Ratton et al. |
| 5,389,078 A | 2/1995 | Zalesky et al. |
| 5,389,091 A | 2/1995 | Moorehead |
| 5,395,324 A | 3/1995 | Hinrichs |
| 5,399,166 A | 3/1995 | Laing |
| 5,403,551 A | 4/1995 | Galloway et al. |
| 5,407,444 A | 4/1995 | Kroll |
| 5,410,908 A | 5/1995 | Erichsen |
| 5,411,685 A | 5/1995 | Burgis |
| 5,415,024 A | 5/1995 | Proffitt et al. |
| 5,418,154 A | 5/1995 | Aebischer et al. |
| 5,421,208 A | 6/1995 | Packard et al. |
| 5,423,743 A | 6/1995 | Butterfield |
| 5,425,374 A | 6/1995 | Ueda et al. |
| 5,425,706 A | 6/1995 | Gross et al. |
| 5,425,742 A | 6/1995 | Joy |
| 5,427,870 A | 6/1995 | Joshi et al. |
| 5,429,483 A | 7/1995 | Tamari |
| 5,429,601 A | 7/1995 | Conley et al. |
| 5,431,171 A | 7/1995 | Harrison et al. |
| 5,431,627 A | 7/1995 | Pastrone et al. |
| 5,433,710 A | 7/1995 | VanAntwerp et al. |
| 5,435,465 A | 7/1995 | El-Amin |
| 5,435,697 A | 7/1995 | Guebeli et al. |
| 5,435,797 A | 7/1995 | Harris |
| 5,438,510 A | 8/1995 | Bryant et al. |
| 5,441,027 A | 8/1995 | Buchanon et al. |
| 5,442,948 A | 8/1995 | Cowing |
| 5,442,950 A | 8/1995 | Unalmiser et al. |
| 5,443,450 A | 8/1995 | Kratoska et al. |
| 5,445,616 A | 8/1995 | Kratoska et al. |
| 5,447,509 A | 9/1995 | Mills et al. |
| 5,447,863 A | 9/1995 | Langley |
| 5,448,034 A | 9/1995 | Skipper et al. |
| 5,448,978 A | 9/1995 | Hasegawa et al. |
| 5,450,750 A | 9/1995 | Abler |
| 5,454,922 A | 10/1995 | Joshi et al. |
| 5,458,469 A | 10/1995 | Hauser |
| 5,460,030 A | 10/1995 | Blosxom et al. |
| 5,460,605 A | 10/1995 | Tuttle et al. |
| 5,460,945 A | 10/1995 | Springer et al. |
| 5,462,525 A | 10/1995 | Srisathapat et al. |
| 5,462,535 A | 10/1995 | Bonnichsen et al. |
| 5,464,392 A | 11/1995 | Epstein et al. |
| 5,464,398 A | 11/1995 | Haindl |
| 5,466,218 A | 11/1995 | Srisathapat et al. |
| 5,466,229 A | 11/1995 | Elson et al. |
| 5,469,846 A | 11/1995 | Khan |
| 5,470,318 A | 11/1995 | Griffith, III et al. |
| 5,472,577 A | 12/1995 | Porter et al. |
| 5,476,444 A | 12/1995 | Keeling et al. |
| 5,476,449 A | 12/1995 | Richmond |
| 5,478,751 A | 12/1995 | Oosta et al. |
| 5,480,381 A | 1/1996 | Weston |
| 5,482,446 A | 1/1996 | Williamson et al. |
| 5,482,745 A | 1/1996 | Cuellar et al. |
| 5,483,930 A | 1/1996 | Moriya et al. |
| 5,485,408 A | 1/1996 | Blomquist |
| 5,487,528 A | 1/1996 | Richmond |
| 5,489,265 A | 2/1996 | Montalvo et al. |
| 5,492,534 A | 2/1996 | Athayde et al. |
| 5,494,578 A | 2/1996 | Brown et al. |
| 5,498,421 A | 3/1996 | Grinstaff et al. |
| 5,503,538 A | 4/1996 | Wiernicki et al. |
| 5,505,709 A | 4/1996 | Funderburk et al. |
| 5,505,777 A | 4/1996 | Ciardella et al. |
| 5,509,294 A | 4/1996 | Gowing |
| 5,510,336 A | 4/1996 | Saven et al. |
| 5,518,730 A | 5/1996 | Fuisz |
| 5,526,675 A | 6/1996 | Ratton |
| 5,527,288 A | 6/1996 | Gross et al. |
| 5,527,307 A | 6/1996 | Srisathapat et al. |
| 5,527,704 A | 6/1996 | Wolf, Jr. et al. |
| 5,531,698 A | 7/1996 | Olsen |
| 5,533,876 A | 7/1996 | Nelson, II |
| 5,538,043 A | 7/1996 | Salazar |
| 5,540,562 A | 7/1996 | Giter |
| 5,544,519 A | 8/1996 | Hammarberg et al. |
| 5,545,252 A | 8/1996 | Hinshaw et al. |
| 5,551,391 A | 9/1996 | Beck et al. |
| 5,551,850 A | 9/1996 | Williamson et al. |
| 5,554,177 A | 9/1996 | Kieval et al. |
| 5,556,421 A | 9/1996 | Prutchi et al. |
| 5,558,638 A | 9/1996 | Evers et al. |
| 5,562,079 A | 10/1996 | Gray, Jr. |
| 5,563,347 A | 10/1996 | Martin et al. |
| 5,566,865 A | 10/1996 | Jouillat et al. |
| 5,567,287 A | 10/1996 | Joshi et al. |
| 5,568,038 A | 10/1996 | Tatsumi |

(56) References Cited

U.S. PATENT DOCUMENTS

| | | |
|---|---|---|
| 5,568,806 A | 10/1996 | Cheney, II et al. |
| 5,568,884 A | 10/1996 | Bruna |
| 5,575,310 A | 11/1996 | Kamen et al. |
| 5,575,632 A | 11/1996 | Morris et al. |
| 5,575,770 A | 11/1996 | Melsky et al. |
| 5,578,005 A | 11/1996 | Sancoff et al. |
| 5,578,832 A | 11/1996 | Trulson et al. |
| 5,582,168 A | 12/1996 | Samuels et al. |
| 5,590,648 A | 1/1997 | Mitchell et al. |
| 5,593,552 A | 1/1997 | Joshi et al. |
| 5,602,040 A | 2/1997 | May et al. |
| 5,603,729 A | 2/1997 | Brown et al. |
| 5,605,701 A | 2/1997 | Bymaster et al. |
| 5,607,418 A | 3/1997 | Arzbaecher |
| 5,615,671 A | 4/1997 | Schoonen et al. |
| 5,616,123 A | 4/1997 | Cheikh |
| 5,616,132 A | 4/1997 | Newman |
| 5,617,650 A | 4/1997 | Grim |
| RE35,501 E | 5/1997 | Ross et al. |
| 5,628,349 A | 5/1997 | Diggins et al. |
| 5,628,624 A | 5/1997 | Nelson, II |
| 5,634,491 A | 6/1997 | Benedict |
| 5,634,779 A | 6/1997 | Eysymontt |
| 5,637,092 A | 6/1997 | Shaw |
| 5,637,095 A | 6/1997 | Nason et al. |
| 5,639,220 A | 6/1997 | Hawakawa |
| 5,639,441 A | 6/1997 | Sievers et al. |
| 5,639,473 A | 6/1997 | Grinstaff et al. |
| 5,641,405 A | 6/1997 | Keshaviah et al. |
| 5,643,773 A | 7/1997 | Aebisher et al. |
| 5,645,526 A | 7/1997 | Flower |
| 5,651,980 A | 7/1997 | Lanza et al. |
| 5,656,032 A | 8/1997 | Kriesel et al. |
| 5,656,501 A | 8/1997 | Yedgar et al. |
| 5,656,503 A | 8/1997 | May et al. |
| 5,658,250 A | 8/1997 | Blomquist |
| 5,659,126 A | 8/1997 | Farber |
| 5,660,150 A | 8/1997 | Anderson et al. |
| 5,665,065 A | 9/1997 | Colman et al. |
| 5,665,070 A | 9/1997 | McPhee |
| 5,669,877 A | 9/1997 | Blomquist |
| 5,671,874 A | 9/1997 | Behar et al. |
| 5,676,651 A | 10/1997 | Larson, Jr. et al. |
| 5,681,435 A | 10/1997 | Joshi et al. |
| 5,688,113 A | 11/1997 | Bareiss et al. |
| 5,688,225 A | 11/1997 | Walker |
| 5,688,232 A | 11/1997 | Flower |
| 5,693,018 A | 12/1997 | Kriesel et al. |
| 5,694,961 A | 12/1997 | Begemann et al. |
| 5,695,464 A | 12/1997 | Viallet |
| 5,702,384 A | 12/1997 | Umeyama et al. |
| 5,704,520 A | 1/1998 | Gross |
| 5,707,212 A | 1/1998 | Matthews |
| 5,707,361 A | 1/1998 | Slettenmark |
| 5,711,989 A | 1/1998 | Ciardella et al. |
| 5,712,795 A | 1/1998 | Layman et al. |
| 5,713,856 A | 2/1998 | Eggers et al. |
| 5,713,858 A | 2/1998 | Heruth et al. |
| 5,718,562 A | 2/1998 | Lawless et al. |
| 5,719,761 A | 2/1998 | Gatti et al. |
| 5,720,241 A | 2/1998 | Gail |
| 5,720,921 A | 2/1998 | Mersol |
| 5,722,367 A | 3/1998 | Izadorek |
| 5,728,396 A | 3/1998 | Peery et al. |
| 5,730,149 A | 3/1998 | Nakayama et al. |
| 5,730,723 A | 3/1998 | Castellano et al. |
| 5,735,818 A | 4/1998 | Kriesel et al. |
| 5,738,650 A | 4/1998 | Gregg |
| 5,740,718 A | 4/1998 | Rathweg |
| 5,741,211 A | 4/1998 | Renirie et al. |
| 5,741,242 A | 4/1998 | Kriesel et al. |
| 5,743,291 A | 4/1998 | Nehm et al. |
| 5,755,683 A | 5/1998 | Houle et al. |
| 5,759,018 A | 6/1998 | Thanscheidt |
| 5,763,267 A | 6/1998 | Kurjan et al. |
| 5,763,398 A | 6/1998 | Bengtsson |
| 5,765,464 A | 6/1998 | Morita |
| 5,765,729 A | 6/1998 | Miller et al. |
| 5,769,615 A | 6/1998 | Giter |
| 5,770,149 A | 6/1998 | Raible |
| 5,770,160 A | 6/1998 | Smith et al. |
| 5,771,770 A | 6/1998 | Muller |
| 5,782,931 A | 7/1998 | Yang et al. |
| 5,785,688 A | 7/1998 | Joshi et al. |
| 5,788,671 A | 8/1998 | Johnson |
| 5,788,682 A | 8/1998 | Maget |
| 5,792,603 A | 8/1998 | Dunkelman et al. |
| 5,794,505 A | 8/1998 | Fischer et al. |
| 5,794,515 A | 8/1998 | Bethke |
| 5,797,867 A | 8/1998 | Guererra et al. |
| 5,800,387 A | 9/1998 | Duffy et al. |
| 5,800,420 A | 9/1998 | Gross et al. |
| 5,803,319 A | 9/1998 | Smith et al. |
| 5,803,917 A | 9/1998 | Butterfield et al. |
| 5,807,315 A | 9/1998 | Van Antwerp et al. |
| 5,807,375 A | 9/1998 | Gross et al. |
| 5,810,737 A | 9/1998 | Dardik |
| 5,810,771 A | 9/1998 | Blomquist |
| 5,814,020 A | 9/1998 | Gross |
| 5,814,100 A | 9/1998 | Carpentier et al. |
| 5,820,587 A | 10/1998 | Place |
| 5,820,589 A | 10/1998 | Torgerson et al. |
| 5,820,622 A | 10/1998 | Gross et al. |
| 5,823,388 A | 10/1998 | Green |
| 5,823,746 A | 10/1998 | Johnson |
| 5,826,621 A | 10/1998 | Jemmott |
| 5,830,175 A | 11/1998 | Flower |
| 5,837,220 A | 11/1998 | Blake et al. |
| 5,837,444 A | 11/1998 | Shah |
| 5,840,071 A | 11/1998 | Kriesel et al. |
| 5,840,770 A | 11/1998 | Hill |
| 5,848,880 A | 12/1998 | Helmig |
| 5,848,990 A | 12/1998 | Cirelli et al. |
| 5,848,991 A | 12/1998 | Gross et al. |
| 5,849,031 A | 12/1998 | Martinez et al. |
| 5,849,737 A | 12/1998 | Chaplan et al. |
| 5,851,198 A | 12/1998 | Castellano et al. |
| 5,851,549 A | 12/1998 | Svec |
| 5,851,985 A | 12/1998 | Tepic et al. |
| 5,854,074 A | 12/1998 | Charlton et al. |
| 5,858,001 A | 1/1999 | Tsals et al. |
| 5,858,201 A | 1/1999 | Atsuka et al. |
| 5,858,388 A | 1/1999 | Grossman et al. |
| 5,858,393 A | 1/1999 | Bymaster et al. |
| 5,859,365 A | 1/1999 | Kataoka et al. |
| 5,860,957 A | 1/1999 | Jacobson et al. |
| 5,863,187 A | 1/1999 | Bensley et al. |
| 5,865,603 A | 2/1999 | Francart, Jr. |
| 5,871,125 A | 2/1999 | Gross |
| 5,871,515 A | 2/1999 | Wiklund et al. |
| 5,873,857 A | 2/1999 | Kriesel |
| 5,876,189 A | 3/1999 | Lukas et al. |
| 5,876,368 A | 3/1999 | Flower |
| 5,876,370 A | 3/1999 | Blomquist |
| 5,877,146 A | 3/1999 | McKenzie et al. |
| 5,877,216 A | 3/1999 | Place et al. |
| 5,878,992 A | 3/1999 | Edwards et al. |
| 5,880,101 A | 3/1999 | Stankov |
| 5,882,494 A | 3/1999 | Van Antwerp et al. |
| 5,883,138 A | 3/1999 | Hershkowitz et al. |
| 5,885,211 A | 3/1999 | Eppstein et al. |
| 5,885,250 A | 3/1999 | Kriesel et al. |
| 5,885,614 A | 3/1999 | Hirsch |
| 5,886,056 A | 3/1999 | Hershkowitz et al. |
| 5,887,793 A | 3/1999 | Kieffer |
| 5,890,413 A | 4/1999 | Bayer et al. |
| 5,891,097 A * | 4/1999 | Saito et al. .................. 604/141 |
| 5,893,708 A | 4/1999 | Nelson, II |
| 5,894,992 A | 4/1999 | Liu et al. |
| 5,895,369 A | 4/1999 | Flower |
| 5,897,530 A | 4/1999 | Jackson |
| 5,902,336 A | 5/1999 | Mishkin |
| 5,903,710 A | 5/1999 | Wefler et al. |
| 5,912,005 A | 6/1999 | Lanza et al. |

(56) References Cited

U.S. PATENT DOCUMENTS

| | | |
|---|---|---|
| 5,916,191 A | 6/1999 | Plunkett et al. |
| 5,919,156 A | 7/1999 | Stropkay et al. |
| 5,919,209 A | 7/1999 | Schouten |
| 5,919,216 A | 7/1999 | Houben et al. |
| 5,924,456 A | 7/1999 | Simon |
| 5,925,629 A | 7/1999 | Place |
| 5,928,194 A | 7/1999 | Maget |
| 5,928,281 A | 7/1999 | Huynh et al. |
| 5,931,814 A | 8/1999 | Alex et al. |
| 5,933,287 A | 8/1999 | Muller |
| 5,935,099 A | 8/1999 | Peterson et al. |
| 5,935,168 A | 8/1999 | Yang et al. |
| 5,935,598 A | 8/1999 | Sage et al. |
| 5,938,636 A | 8/1999 | Kramer |
| 5,938,640 A | 8/1999 | Maget |
| 5,941,846 A | 8/1999 | Duffy et al. |
| 5,944,694 A | 8/1999 | Hitchins |
| 5,948,367 A | 9/1999 | Gmeiner et al. |
| 5,950,879 A | 9/1999 | Ritsche |
| 5,951,523 A | 9/1999 | Osterlund et al. |
| 5,954,696 A | 9/1999 | Ryan |
| 5,954,697 A | 9/1999 | Srisathapat et al. |
| 5,954,700 A | 9/1999 | Kovelman |
| 5,954,752 A | 9/1999 | Mongeon et al. |
| 5,957,861 A | 9/1999 | Combs et al. |
| 5,957,885 A | 9/1999 | Bollish et al. |
| 5,957,889 A | 9/1999 | Poulson et al. |
| 5,957,895 A | 9/1999 | Sage et al. |
| 5,958,760 A | 9/1999 | Freeman |
| 5,961,305 A | 10/1999 | Eek et al. |
| 5,961,483 A | 10/1999 | Sage et al. |
| 5,962,566 A | 10/1999 | Grandfilis et al. |
| 5,964,724 A | 10/1999 | Rivera et al. |
| 5,973,012 A | 10/1999 | Behrmann et al. |
| 5,980,596 A | 11/1999 | Hershkowitz et al. |
| 5,983,976 A | 11/1999 | Kono |
| 5,984,894 A | 11/1999 | Poulsen et al. |
| 5,984,897 A | 11/1999 | Peterson et al. |
| 5,984,906 A | 11/1999 | Bonnichsen et al. |
| 5,985,305 A | 11/1999 | Peery et al. |
| 5,988,165 A | 11/1999 | Richey et al. |
| 5,988,998 A | 11/1999 | Glover |
| 5,989,238 A | 11/1999 | Ginsburg |
| 5,992,695 A | 11/1999 | Start |
| 5,997,501 A | 12/1999 | Gross et al. |
| 5,997,518 A | 12/1999 | Laibovitz et al. |
| 6,001,585 A | 12/1999 | Gramer |
| 6,003,736 A | 12/1999 | Ljunggren |
| 6,006,800 A | 12/1999 | Nakano |
| 6,007,314 A | 12/1999 | Nelson, II |
| 6,012,492 A | 1/2000 | Kozyuk |
| 6,013,020 A | 1/2000 | Meloul et al. |
| 6,016,044 A | 1/2000 | Holdaway |
| 6,017,318 A | 1/2000 | Gauthier |
| 6,017,545 A | 1/2000 | Modi |
| 6,023,641 A | 2/2000 | Thompson |
| 6,024,009 A | 2/2000 | Morita |
| 6,024,539 A | 2/2000 | Blomquist |
| 6,030,358 A | 2/2000 | Odland |
| 6,033,377 A | 3/2000 | Rasmussen et al. |
| 6,034,054 A | 3/2000 | DeFelippis et al. |
| 6,035,639 A | 3/2000 | Kolmanovsky |
| 6,037,346 A | 3/2000 | Doherty, Jr. et al. |
| 6,038,960 A | 3/2000 | Fukushima et al. |
| 6,042,561 A | 3/2000 | Ash et al. |
| 6,048,337 A | 4/2000 | Svedman |
| 6,051,256 A | 4/2000 | Platz et al. |
| 6,056,522 A | 5/2000 | Johnson |
| 6,059,507 A | 5/2000 | Adams |
| 6,059,753 A | 5/2000 | Faust et al. |
| 6,062,022 A | 5/2000 | Folsom et al. |
| 6,062,531 A | 5/2000 | Rapp et al. |
| 6,063,053 A | 5/2000 | Castellano et al. |
| 6,065,279 A | 5/2000 | Kuromitsu et al. |
| 6,065,289 A | 5/2000 | Phillips |
| 6,065,941 A | 5/2000 | Gray et al. |
| 6,071,423 A | 6/2000 | Brown et al. |
| 6,073,048 A | 6/2000 | Kieval et al. |
| 6,074,359 A | 6/2000 | Keshaviah et al. |
| 6,077,246 A | 6/2000 | Kullas et al. |
| 6,080,130 A | 6/2000 | Castellano et al. |
| 6,083,602 A | 7/2000 | Caldwell et al. |
| 6,083,710 A | 7/2000 | Heller et al. |
| 6,086,562 A | 7/2000 | Jacobson et al. |
| 6,093,167 A | 7/2000 | Houben et al. |
| 6,093,312 A | 7/2000 | Boulter |
| 6,095,134 A | 8/2000 | Sievers et al. |
| 6,096,216 A | 8/2000 | Shanbrom et al. |
| 6,099,293 A | 8/2000 | Kern et al. |
| 6,099,495 A | 8/2000 | Kinghorn et al. |
| 6,099,504 A | 8/2000 | Gross et al. |
| 6,102,127 A | 8/2000 | Pierce |
| 6,103,033 A | 8/2000 | Say et al. |
| 6,103,275 A | 8/2000 | Seitz et al. |
| 6,106,477 A | 8/2000 | Miesel et al. |
| 6,109,896 A | 8/2000 | Schuller et al. |
| 6,110,148 A | 8/2000 | Brown et al. |
| 6,110,152 A | 8/2000 | Kovelman |
| 6,110,427 A | 8/2000 | Uffenheimer |
| RE36,871 E | 9/2000 | Epstein et al. |
| 6,113,782 A | 9/2000 | Leonard |
| 6,120,460 A | 9/2000 | Abreu |
| 6,122,536 A | 9/2000 | Sun et al. |
| 6,123,175 A | 9/2000 | Fett |
| 6,123,686 A | 9/2000 | Olsen et al. |
| 6,126,956 A | 10/2000 | Grossman et al. |
| 6,127,363 A | 10/2000 | Doherty, Jr. et al. |
| 6,132,686 A | 10/2000 | Gallup et al. |
| 6,135,196 A | 10/2000 | Kono |
| 6,135,978 A | 10/2000 | Houben et al. |
| D433,755 S | 11/2000 | Mastrotaro et al. |
| 6,142,939 A | 11/2000 | Eppstein et al. |
| 6,143,238 A | 11/2000 | Konishi et al. |
| 6,143,252 A | 11/2000 | Haxo, Jr. et al. |
| 6,144,866 A | 11/2000 | Miesel et al. |
| 6,145,625 A | 11/2000 | Prokop et al. |
| 6,147,070 A | 11/2000 | Facchini |
| 6,147,109 A | 11/2000 | Liao et al. |
| 6,152,898 A | 11/2000 | Olsen |
| 6,155,748 A | 12/2000 | Allen et al. |
| 6,156,753 A | 12/2000 | Doherty, Jr. et al. |
| 6,158,431 A | 12/2000 | Poole |
| 6,158,965 A | 12/2000 | Butterfield et al. |
| 6,163,721 A | 12/2000 | Thompson |
| 6,164,924 A | 12/2000 | Gruett et al. |
| 6,165,155 A | 12/2000 | Jacobson et al. |
| 6,167,290 A | 12/2000 | Yang et al. |
| 6,168,575 B1 | 1/2001 | Soultanpour |
| 6,175,752 B1 | 1/2001 | Say et al. |
| 6,176,692 B1 | 1/2001 | Reinartz et al. |
| 6,178,996 B1 | 1/2001 | Suzuki |
| 6,179,583 B1 | 1/2001 | Weston |
| 6,180,597 B1 | 1/2001 | Liao et al. |
| 6,185,460 B1 | 2/2001 | Thompson |
| 6,186,982 B1 | 2/2001 | Gross et al. |
| 6,198,383 B1 | 3/2001 | Sekura et al. |
| 6,205,961 B1 | 3/2001 | Bailey et al. |
| 6,210,135 B1 | 4/2001 | Rassin et al. |
| 6,210,361 B1 | 4/2001 | Kamen et al. |
| 6,210,957 B1 | 4/2001 | Carpentier et al. |
| 6,211,147 B1 | 4/2001 | Unemori |
| 6,211,426 B1 | 4/2001 | Abrams |
| 6,212,948 B1 | 4/2001 | Ekdahl et al. |
| 6,213,120 B1 | 4/2001 | Block et al. |
| 6,217,826 B1 | 4/2001 | Reeder et al. |
| 6,218,666 B1 | 4/2001 | Lukica et al. |
| 6,221,378 B1 | 4/2001 | Modi |
| 6,223,080 B1 | 4/2001 | Thompson |
| 6,223,703 B1 | 5/2001 | Galvin |
| 6,223,746 B1 | 5/2001 | Jewett et al. |
| 6,224,347 B1 | 5/2001 | Clark et al. |
| 6,224,352 B1 | 5/2001 | Hauser et al. |
| 6,227,818 B1 | 5/2001 | Falk et al. |
| 6,228,044 B1 | 5/2001 | Jensen et al. |

(56) References Cited

U.S. PATENT DOCUMENTS

| | | |
|---|---|---|
| 6,229,584 B1 | 5/2001 | Chuo et al. |
| 6,231,882 B1 | 5/2001 | Modi |
| 6,232,609 B1 | 5/2001 | Snyder et al. |
| 6,236,887 B1 | 5/2001 | Ben-Hamin et al. |
| 6,238,423 B1 | 5/2001 | Bardy |
| 6,241,704 B1 | 6/2001 | Peterson et al. |
| 6,241,743 B1 | 6/2001 | Levin et al. |
| 6,245,347 B1 | 6/2001 | Zhang et al. |
| 6,247,493 B1 | 6/2001 | Henderson |
| 6,248,067 B1 | 6/2001 | Causey, III et al. |
| 6,248,093 B1 | 6/2001 | Moberg |
| 6,248,280 B1 | 6/2001 | Kern et al. |
| 6,251,293 B1 | 6/2001 | Snodgrass et al. |
| 6,251,932 B1 | 6/2001 | Reicht et al. |
| 6,254,355 B1 | 7/2001 | Gharib |
| 6,256,533 B1 | 7/2001 | Yuzhakov et al. |
| 6,257,178 B1 | 7/2001 | Laimbock |
| 6,257,191 B1 | 7/2001 | Kutlucinar |
| 6,261,272 B1 | 7/2001 | Gross et al. |
| 6,261,280 B1 | 7/2001 | Houbin et al. |
| 6,264,439 B1 | 7/2001 | Falk et al. |
| 6,264,680 B1 | 7/2001 | Ash et al. |
| 6,266,564 B1 | 7/2001 | Hill et al. |
| 6,270,478 B1 | 8/2001 | Mernoe |
| 6,275,717 B1 | 8/2001 | Gross et al. |
| 6,276,434 B1 | 8/2001 | Kono |
| 6,277,819 B1 | 8/2001 | Efendic |
| 6,280,408 B1 | 8/2001 | Sipin |
| 6,280,409 B1 | 8/2001 | Stone et al. |
| 6,280,416 B1 | 8/2001 | Van Antwerp et al. |
| 6,283,197 B1 | 9/2001 | Kono |
| 6,283,680 B1 | 9/2001 | Vidal |
| 6,283,944 B1 | 9/2001 | McMullen et al. |
| 6,283,949 B1 | 9/2001 | Roorda |
| 6,284,725 B1 | 9/2001 | Coolidge et al. |
| 6,288,518 B1 | 9/2001 | Yang et al. |
| 6,293,242 B1 | 9/2001 | Kutlucinar |
| 6,293,429 B2 | 9/2001 | Sadler et al. |
| 6,294,550 B1 | 9/2001 | Place et al. |
| 6,296,456 B1 | 10/2001 | Thornelow et al. |
| 6,298,941 B1 | 10/2001 | Spadafora |
| 6,299,415 B1 | 10/2001 | Bahrton |
| 6,302,107 B1 | 10/2001 | Richey et al. |
| 6,302,653 B1 | 10/2001 | Bryant et al. |
| 6,302,855 B1 | 10/2001 | Lav et al. |
| 6,306,420 B1 | 10/2001 | Cheikh |
| 6,306,841 B1 | 10/2001 | Place et al. |
| 6,310,270 B1 | 10/2001 | Huang et al. |
| 6,312,409 B1 | 11/2001 | Gross |
| 6,314,317 B1 | 11/2001 | Willis |
| 6,315,769 B1 | 11/2001 | Peer et al. |
| 6,319,215 B1 | 11/2001 | Manor et al. |
| 6,319,245 B1 | 11/2001 | Berrigan |
| 6,323,022 B1 | 11/2001 | Chang et al. |
| 6,325,999 B1 | 12/2001 | Bellgrau et al. |
| 6,327,964 B1 | 12/2001 | Schuller et al. |
| 6,328,004 B1 | 12/2001 | Rynhart |
| 6,331,172 B1 | 12/2001 | Epstein et al. |
| 6,334,761 B1 | 1/2002 | Tai et al. |
| 6,338,942 B2 | 1/2002 | Kraus et al. |
| 6,340,783 B1 | 1/2002 | Snow |
| 6,342,037 B1 | 1/2002 | Roe et al. |
| 6,342,484 B1 | 1/2002 | Kulkarni et al. |
| 6,344,457 B1 | 2/2002 | Jeanpetit et al. |
| 6,346,095 B1 | 2/2002 | Gross et al. |
| 6,350,589 B1 | 2/2002 | Morris et al. |
| 6,355,030 B1 | 3/2002 | Aldrich et al. |
| 6,358,519 B1 | 3/2002 | Waterman |
| 6,364,865 B1 | 4/2002 | Lavi et al. |
| 6,365,185 B1 | 4/2002 | Ritchel et al. |
| 6,365,628 B1 | 4/2002 | Berge |
| 6,366,808 B1 | 4/2002 | Schroppel et al. |
| 6,368,272 B1 | 4/2002 | Porumbescu |
| 6,371,732 B1 | 4/2002 | Moubayed et al. |
| 6,372,182 B1 | 4/2002 | Mauro et al. |
| 6,372,508 B1 | 4/2002 | Schnizer et al. |
| 6,374,683 B1 | 4/2002 | Hunicke-Smith et al. |
| 6,381,493 B1 | 4/2002 | Stadler et al. |
| 6,382,923 B1 | 5/2002 | gray |
| 6,393,893 B1 | 5/2002 | Fetz et al. |
| 6,395,292 B2 | 5/2002 | Peery et al. |
| 6,395,536 B2 | 5/2002 | Freeman |
| 6,397,199 B1 | 5/2002 | Goodwin, III |
| 6,398,718 B1 | 6/2002 | Yachia et al. |
| 6,398,760 B1 | 6/2002 | Danby |
| 6,399,024 B1 | 6/2002 | Bevirt et al. |
| 6,402,689 B1 | 6/2002 | Scarantino et al. |
| 6,406,455 B1 | 6/2002 | Willis et al. |
| 6,409,698 B1 | 6/2002 | Robinson |
| 6,412,273 B1 | 7/2002 | Rohs |
| 6,413,238 B1 | 7/2002 | Maget |
| 6,413,254 B1 | 7/2002 | Hissong et al. |
| 6,415,961 B2 | 7/2002 | Bonnigue |
| 6,416,215 B1 | 7/2002 | Terentiev |
| 6,416,291 B1 | 7/2002 | Butterfield et al. |
| 6,416,293 B1 | 7/2002 | Bouchard et al. |
| 6,420,169 B1 | 7/2002 | Read et al. |
| 6,422,256 B1 | 7/2002 | Balazy et al. |
| 6,423,029 B1 | 7/2002 | Elsberry |
| 6,423,035 B1 | 7/2002 | Das et al. |
| 6,423,344 B1 | 7/2002 | Platz et al. |
| 6,425,740 B1 | 7/2002 | Jacobsen et al. |
| 6,427,088 B1 | 7/2002 | Bowman, IV et al. |
| 6,428,491 B1 | 8/2002 | Weiss |
| 6,429,197 B1 | 8/2002 | Coolidge et al. |
| 6,429,230 B1 | 8/2002 | Cavazza |
| 6,429,232 B1 | 8/2002 | Kinsella et al. |
| 6,433,040 B1 | 8/2002 | Dellamary et al. |
| 6,436,072 B1 | 8/2002 | Kullas et al. |
| 6,436,078 B1 | 8/2002 | Svedman |
| 6,438,408 B1 | 8/2002 | Mulligan et al. |
| 6,440,096 B1 | 8/2002 | Lastovich et al. |
| 6,441,036 B1 | 8/2002 | Berge |
| 6,443,097 B1 | 9/2002 | Zohar et al. |
| 6,443,942 B2 | 9/2002 | Van Antwerp |
| 6,446,513 B1 | 9/2002 | Henderson |
| 6,447,443 B1 | 9/2002 | Keogh et al. |
| 6,447,446 B1 | 9/2002 | Smith et al. |
| 6,447,475 B1 | 9/2002 | Castellano et al. |
| 6,447,522 B2 | 9/2002 | Gambale et al. |
| 6,450,942 B1 | 9/2002 | Lapanashvili et al. |
| 6,454,707 B1 | 9/2002 | Casscells, III |
| 6,454,785 B2 | 9/2002 | De Hoyos Garza |
| 6,457,956 B1 | 10/2002 | Hauser et al. |
| 6,458,102 B1 | 10/2002 | Mann et al. |
| 6,458,109 B1 | 10/2002 | Henley et al. |
| 6,458,256 B1 | 10/2002 | Zhong |
| 6,458,762 B1 | 10/2002 | McKenzie et al. |
| 6,461,329 B1 | 10/2002 | Van Antwerp et al. |
| 6,461,331 B1 | 10/2002 | Van Antwerp |
| 6,461,334 B1 | 10/2002 | Buch-Rasmussen et al. |
| 6,461,828 B1 | 10/2002 | Stanton et al. |
| 6,463,794 B1 | 10/2002 | Moshe et al. |
| 6,464,667 B1 | 10/2002 | Kamen et al. |
| 6,467,267 B2 | 10/2002 | Kanazawa et al. |
| 6,468,200 B1 | 10/2002 | Fischi |
| 6,469,016 B1 | 10/2002 | Place et al. |
| 6,471,496 B1 | 10/2002 | Merklein et al. |
| 6,471,689 B1 | 10/2002 | Joseph et al. |
| 6,471,855 B1 | 10/2002 | Odak et al. |
| 6,472,434 B1 | 10/2002 | Place et al. |
| 6,474,219 B2 | 11/2002 | Klitmose et al. |
| 6,475,180 B2 | 11/2002 | Peterson et al. |
| 6,475,750 B1 | 11/2002 | Han et al. |
| 6,477,774 B1 | 11/2002 | Marando et al. |
| 6,478,385 B1 | 11/2002 | Nishii et al. |
| 6,478,771 B1 | 11/2002 | Lavi et al. |
| 6,482,186 B1 | 11/2002 | Douglas et al. |
| 6,484,906 B2 | 11/2002 | Bonnigue |
| 6,485,263 B1 | 11/2002 | Bryant et al. |
| 6,485,452 B1 | 11/2002 | French et al. |
| 6,485,461 B1 | 11/2002 | Mason et al. |
| 6,488,652 B1 | 12/2002 | Weijand et al. |
| 6,488,697 B1 | 12/2002 | Ariura et al. |

(56) References Cited

U.S. PATENT DOCUMENTS

| | | |
|---|---|---|
| 6,489,346 B1 | 12/2002 | Phillips |
| 6,490,483 B2 | 12/2002 | Willis |
| 6,494,865 B1 | 12/2002 | Alchas |
| 6,500,150 B1 | 12/2002 | Gross et al. |
| 6,505,059 B1 | 1/2003 | Kollias et al. |
| 6,506,594 B1 | 1/2003 | Barany et al. |
| 6,508,788 B2 | 1/2003 | Preuthun |
| 6,511,435 B1 | 1/2003 | Bluth et al. |
| 6,512,949 B1 | 1/2003 | Combs et al. |
| 6,514,689 B2 | 2/2003 | Han et al. |
| 6,517,482 B1 | 2/2003 | Elden et al. |
| 6,522,980 B1 | 2/2003 | Arnold |
| 6,530,900 B1 | 3/2003 | Daily et al. |
| 6,533,183 B2 | 3/2003 | Aasmul et al. |
| 6,537,241 B1 | 3/2003 | Odland |
| 6,537,251 B2 | 3/2003 | Klitmose |
| 6,537,268 B1 | 3/2003 | Gibson et al. |
| 6,537,272 B2 | 3/2003 | Christopherson et al. |
| 6,540,006 B2 | 4/2003 | Kono |
| 6,540,161 B1 | 4/2003 | Gordon |
| 6,540,727 B2 | 4/2003 | Harper et al. |
| 6,540,996 B1 | 4/2003 | Zwaal et al. |
| 6,541,021 B1 | 4/2003 | Johnson et al. |
| 6,542,774 B2 | 4/2003 | Hill et al. |
| 6,542,775 B2 | 4/2003 | Ding et al. |
| 6,544,212 B2 | 4/2003 | Galley et al. |
| 6,550,245 B2 | 4/2003 | Nishii et al. |
| 6,551,276 B1 | 4/2003 | Mann et al. |
| 6,551,992 B1 | 4/2003 | DeFelippis et al. |
| 6,553,245 B1 | 4/2003 | Grace et al. |
| 6,554,798 B1 | 4/2003 | Mann et al. |
| 6,557,454 B2 | 5/2003 | Miyazawa |
| 6,558,320 B1 | 5/2003 | Causey et al. |
| 6,558,345 B1 | 5/2003 | Houben et al. |
| 6,558,351 B1 | 5/2003 | Steil et al. |
| 6,558,665 B1 | 5/2003 | Cohen et al. |
| 6,558,902 B1 | 5/2003 | Hillenkamp |
| 6,560,478 B1 | 5/2003 | Alfano et al. |
| 6,562,001 B2 | 5/2003 | Lebel et al. |
| 6,564,093 B1 | 5/2003 | Ostrow et al. |
| 6,564,104 B2 | 5/2003 | Nelson et al. |
| 6,564,105 B2 | 5/2003 | Starkweather et al. |
| 6,565,802 B1 | 5/2003 | Hanley et al. |
| 6,565,872 B2 | 5/2003 | Wu et al. |
| 6,568,898 B2 | 5/2003 | Nishimura et al. |
| 6,568,922 B1 | 5/2003 | Winsel |
| 6,569,123 B2 | 5/2003 | Alchas et al. |
| 6,569,143 B2 | 5/2003 | Alchas et al. |
| 6,569,456 B2 | 5/2003 | Faour et al. |
| 6,571,128 B2 | 5/2003 | Lebel et al. |
| 6,571,831 B1 | 6/2003 | Hart |
| 6,572,542 B1 | 6/2003 | Houben et al. |
| 6,572,566 B2 | 6/2003 | Effenhauser |
| 6,577,899 B2 | 6/2003 | Lebel et al. |
| 6,579,496 B1 | 6/2003 | Fausset et al. |
| 6,582,366 B1 | 6/2003 | Porumbescu |
| 6,582,393 B2 | 6/2003 | Sage, Jr. |
| 6,582,418 B1 | 6/2003 | Verbeek et al. |
| 6,583,111 B1 | 6/2003 | DiMarchi et al. |
| 6,585,644 B2 | 7/2003 | Lebel et al. |
| 6,585,707 B2 | 7/2003 | Cabiri et al. |
| 6,589,158 B2 | 7/2003 | Winkler |
| 6,589,229 B1 | 7/2003 | Connelly et al. |
| 6,592,544 B1 | 7/2003 | Mooney et al. |
| 6,592,571 B1 | 7/2003 | Verbeek et al. |
| 6,592,860 B1 | 7/2003 | Levy et al. |
| 6,592,904 B2 | 7/2003 | Platz et al. |
| 6,593,313 B2 | 7/2003 | Place et al. |
| 6,595,756 B2 | 7/2003 | Gray et al. |
| 6,595,948 B2 | 7/2003 | Suzuki et al. |
| 6,595,956 B1 | 7/2003 | Gross et al. |
| 6,599,281 B1 | 7/2003 | Struys et al. |
| 6,602,241 B2 | 8/2003 | Makower et al. |
| 6,604,908 B1 | 8/2003 | Bryant et al. |
| 6,605,072 B2 | 8/2003 | Struys et al. |
| 6,607,513 B1 | 8/2003 | Down et al. |
| 6,607,658 B1 | 8/2003 | Heller et al. |
| 6,607,739 B1 | 8/2003 | Wallo |
| 6,610,003 B1 | 8/2003 | Meloul et al. |
| 6,612,535 B1 | 9/2003 | Tai et al. |
| 6,613,019 B2 | 9/2003 | Munk |
| 6,616,196 B1 | 9/2003 | Weh et al. |
| 6,616,627 B2 | 9/2003 | Willis et al. |
| 6,618,603 B2 | 9/2003 | Varalli et al. |
| 6,620,140 B1 | 9/2003 | Metzger |
| 6,620,379 B1 | 9/2003 | Piuk et al. |
| 6,623,698 B2 | 9/2003 | Kuo |
| 6,626,644 B2 | 9/2003 | Ozaki |
| 6,629,934 B2 | 10/2003 | Mault et al. |
| 6,629,938 B1 | 10/2003 | Engvall et al. |
| 6,629,949 B1 | 10/2003 | Douglas |
| 6,634,939 B2 | 10/2003 | Johnson |
| 6,635,014 B2 | 10/2003 | Starkweather et al. |
| 6,636,796 B2 | 10/2003 | Kolmanovsky et al. |
| 6,639,381 B2 | 10/2003 | Tamura et al. |
| 6,641,533 B2 | 11/2003 | Causey et al. |
| 6,641,562 B1 * | 11/2003 | Peterson ................. 604/141 |
| 6,641,565 B1 | 11/2003 | Lavi et al. |
| 6,641,566 B2 | 11/2003 | Douglas et al. |
| 6,642,019 B1 | 11/2003 | Anderson et al. |
| 6,645,181 B1 | 11/2003 | Lavi et al. |
| 6,648,821 B2 | 11/2003 | Lebel et al. |
| 6,648,859 B2 | 11/2003 | Bitdinger et al. |
| 6,648,861 B2 | 11/2003 | Platt et al. |
| 6,649,403 B1 | 11/2003 | McDevitt et al. |
| 6,650,919 B2 | 11/2003 | Edelberg et al. |
| 6,651,546 B2 | 11/2003 | Sandlin |
| 6,656,148 B2 | 12/2003 | Das et al. |
| 6,656,158 B2 | 12/2003 | Manhoney et al. |
| 6,656,159 B2 | 12/2003 | Flaherty et al. |
| 6,663,359 B2 | 12/2003 | Gray |
| 6,666,821 B2 | 12/2003 | Keimel |
| 6,668,701 B1 | 12/2003 | Everitt |
| 6,669,663 B1 | 12/2003 | Thompson |
| 6,669,669 B2 | 12/2003 | Flaherty et al. |
| 6,676,387 B1 | 1/2004 | Penn |
| 6,677,320 B2 | 1/2004 | Diederich et al. |
| 6,682,497 B2 | 1/2004 | Jensen et al. |
| 6,683,690 B1 | 1/2004 | Tobias |
| 6,689,100 B2 | 2/2004 | Connelly et al. |
| 6,689,108 B2 | 2/2004 | Lavi et al. |
| 6,689,118 B2 | 2/2004 | Alchas et al. |
| 6,689,373 B2 | 2/2004 | Johnson et al. |
| 6,692,456 B1 | 2/2004 | Eppstein et al. |
| 6,692,457 B2 | 2/2004 | Flaherty et al. |
| 6,694,191 B2 | 2/2004 | Starkweather et al. |
| 6,695,011 B2 | 2/2004 | Sochtig |
| 6,696,090 B1 | 2/2004 | Nilsson et al. |
| 6,696,493 B2 | 2/2004 | Cavazza |
| 6,699,218 B2 | 3/2004 | Flaherty et al. |
| 6,699,234 B2 | 3/2004 | Yeh et al. |
| 6,699,885 B2 | 3/2004 | Phillips |
| 6,702,779 B2 | 3/2004 | Connelly et al. |
| 6,702,857 B2 | 3/2004 | Brauker et al. |
| 6,705,845 B2 | 3/2004 | Krieger et al. |
| 6,706,008 B2 | 3/2004 | Vishnoi et al. |
| 6,706,009 B2 | 3/2004 | Diermann et al. |
| 6,706,689 B2 | 3/2004 | Coolidge et al. |
| 6,710,051 B1 | 3/2004 | Trier |
| 6,711,489 B2 | 3/2004 | Haskara et al. |
| 6,712,095 B2 | 3/2004 | Williamson et al. |
| 6,715,516 B2 | 4/2004 | Ohms et al. |
| 6,716,190 B1 | 4/2004 | Glines et al. |
| 6,718,206 B2 | 4/2004 | Casavante |
| 6,719,302 B2 | 4/2004 | Andrick |
| 6,723,068 B2 | 4/2004 | Lavi et al. |
| 6,723,072 B2 | 4/2004 | Flaherty et al. |
| 6,726,920 B1 | 4/2004 | Theeuwes et al. |
| 6,732,573 B2 | 5/2004 | Shin et al. |
| 6,733,446 B2 | 5/2004 | Lebel et al. |
| 6,734,186 B1 | 5/2004 | Maw et al. |
| 6,736,796 B2 | 5/2004 | Shekalim et al. |
| 6,738,663 B2 | 5/2004 | Schroppel et al. |
| 6,738,707 B2 | 5/2004 | Kotwicki et al. |

(56) References Cited

U.S. PATENT DOCUMENTS

| | | |
|---|---|---|
| 6,740,059 B2 | 5/2004 | Flaherty et al. |
| 6,740,072 B2 | 5/2004 | Starkweather et al. |
| 6,740,075 B2 | 5/2004 | Lebel et al. |
| 6,743,201 B1 | 6/2004 | Doing et al. |
| 6,743,202 B2 | 6/2004 | Hirschman et al. |
| 6,744,152 B2 | 6/2004 | Kroll |
| 6,745,079 B2 | 6/2004 | King |
| 6,746,438 B1 | 6/2004 | Arnissolle |
| 6,748,930 B2 | 6/2004 | Bofinger et al. |
| 6,749,403 B2 | 6/2004 | Bryant et al. |
| 6,749,587 B2 | 6/2004 | Flaherty et al. |
| 6,752,785 B2 | 6/2004 | Van Antwerp et al. |
| 6,752,787 B1 | 6/2004 | Causey et al. |
| 6,755,628 B1 | 6/2004 | Howell |
| 6,758,593 B1 | 7/2004 | Terentiev |
| 6,759,386 B2 | 7/2004 | Franco |
| 6,767,188 B2 | 7/2004 | Vrane et al. |
| 6,767,896 B1 | 7/2004 | McIntosh et al. |
| 6,768,425 B2 | 7/2004 | Flaherty et al. |
| 6,769,384 B2 | 8/2004 | Dougherty |
| 6,770,054 B1 | 8/2004 | Smolyarov et al. |
| 6,773,669 B1 | 8/2004 | Holaday et al. |
| 6,773,739 B2 | 8/2004 | Hauck et al. |
| 6,776,776 B2 | 8/2004 | Alchas et al. |
| 6,780,156 B2 | 8/2004 | Haueter et al. |
| 6,780,171 B2 | 8/2004 | Gabel et al. |
| 6,780,426 B2 | 8/2004 | Zhang et al. |
| 6,780,770 B2 | 8/2004 | Larson |
| 6,780,836 B2 | 8/2004 | Unemori |
| 6,783,107 B2 | 8/2004 | Chatufale |
| 6,783,328 B2 | 8/2004 | Lucke et al. |
| 6,786,246 B2 | 9/2004 | Ohms et al. |
| 6,790,670 B2 | 9/2004 | Munagavalasa et al. |
| 6,796,956 B2 | 9/2004 | Hartlaub et al. |
| 6,801,420 B2 | 10/2004 | Talbot et al. |
| 6,804,002 B2 | 10/2004 | Fine et al. |
| 6,804,555 B2 | 10/2004 | Warkentin |
| 6,805,122 B2 | 10/2004 | Richey et al. |
| 6,805,687 B2 | 10/2004 | Dextradeur et al. |
| 6,808,506 B2 | 10/2004 | Lastovich et al. |
| 6,810,290 B2 | 10/2004 | Lebel et al. |
| RE38,654 E | 11/2004 | Hill et al. |
| 6,811,534 B2 | 11/2004 | Bowman et al. |
| 6,811,792 B2 | 11/2004 | Roser et al. |
| 6,813,519 B2 | 11/2004 | Lebel et al. |
| 6,813,964 B1 | 11/2004 | Clark et al. |
| 6,821,249 B2 | 11/2004 | Casscells et al. |
| 6,821,484 B1 | 11/2004 | Gregersen |
| 6,824,529 B2 | 11/2004 | Gross et al. |
| 6,827,524 B2 | 12/2004 | Starry, Jr. et al. |
| 6,827,702 B2 | 12/2004 | Lebel et al. |
| 6,827,710 B1 | 12/2004 | Mooney et al. |
| 6,827,898 B1 | 12/2004 | Fausset et al. |
| 6,828,552 B2 | 12/2004 | Hartley |
| 6,830,558 B2 | 12/2004 | Flaherty et al. |
| 6,830,560 B1 | 12/2004 | Gross et al. |
| 6,835,175 B1 | 12/2004 | Porumbescu |
| 6,835,194 B2 | 12/2004 | Johnson et al. |
| 6,842,642 B2 | 1/2005 | Vanhout |
| 6,843,782 B2 | 1/2005 | Gross et al. |
| 6,847,898 B1 | 1/2005 | Chen et al. |
| 6,851,449 B2 | 2/2005 | Kleibrink |
| 6,852,104 B2 | 2/2005 | Blomquist |
| 6,852,487 B1 | 2/2005 | Barany et al. |
| 6,854,432 B2 | 2/2005 | Hirano |
| 6,854,620 B2 | 2/2005 | Ramey |
| 6,858,011 B2 | 2/2005 | Sehgal |
| 6,858,403 B2 | 2/2005 | Han et al. |
| 6,864,101 B1 | 3/2005 | Winkler et al. |
| 6,867,196 B1 | 3/2005 | Wolff et al. |
| 6,868,358 B2 | 3/2005 | Brown |
| 6,872,200 B2 | 3/2005 | Mann et al. |
| 6,873,268 B2 | 3/2005 | Lebel et al. |
| 6,876,885 B2 | 4/2005 | Swoyer et al. |
| 6,877,713 B1 | 4/2005 | Gray et al. |
| 6,880,564 B2 | 4/2005 | Erickson |
| 6,884,122 B2 | 4/2005 | Robinson et al. |
| 6,884,228 B2 | 4/2005 | Brown et al. |
| 6,885,881 B2 | 4/2005 | Leonhardt |
| 6,885,888 B2 | 4/2005 | Rezai |
| 6,886,556 B2 | 5/2005 | Fuchs |
| 6,892,755 B2 | 5/2005 | Black |
| 6,892,900 B2 | 5/2005 | Drechsel |
| 6,894,024 B2 | 5/2005 | Coolidge et al. |
| 6,896,666 B2 | 5/2005 | Kochamba |
| 6,899,699 B2 | 5/2005 | Enggaard |
| RE38,749 E | 6/2005 | Dardik |
| 6,905,479 B1 | 6/2005 | Bouchard et al. |
| 6,906,028 B2 | 6/2005 | DeFelippis et al. |
| 6,908,591 B2 | 6/2005 | MacPhee et al. |
| 6,909,840 B2 | 6/2005 | Harwig et al. |
| 6,912,425 B2 | 6/2005 | Nova et al. |
| 6,913,933 B2 | 7/2005 | Jacobs et al. |
| 6,914,076 B2 | 7/2005 | Cavazza |
| 6,916,159 B2 | 7/2005 | Rush et al. |
| 6,918,542 B2 | 7/2005 | Silverbrook et al. |
| 6,923,006 B2 | 8/2005 | Walton |
| 6,923,180 B2 | 8/2005 | Richey et al. |
| 6,923,764 B2 | 8/2005 | Aceti et al. |
| 6,926,694 B2 | 8/2005 | Marano-Ford et al. |
| 6,930,093 B2 | 8/2005 | Brantl |
| 6,931,845 B2 | 8/2005 | Schaeffer |
| 6,931,925 B2 | 8/2005 | Huemer et al. |
| 6,932,114 B2 | 8/2005 | Sparks |
| 6,932,796 B2 | 8/2005 | Sage et al. |
| 6,935,531 B1 | 8/2005 | Clayton |
| 6,935,539 B2 | 8/2005 | Krieger et al. |
| 6,936,026 B2 | 8/2005 | Diermann et al. |
| 6,936,029 B2 | 8/2005 | Mann et al. |
| 6,936,046 B2 | 8/2005 | Hissong et al. |
| 6,939,323 B2 | 9/2005 | Angel et al. |
| 6,939,324 B2 | 9/2005 | Gonnelli et al. |
| 6,942,636 B2 | 9/2005 | Holst et al. |
| 6,943,034 B1 | 9/2005 | Winkler et al. |
| 6,946,117 B1 | 9/2005 | Schutt et al. |
| 6,948,918 B2 | 9/2005 | Hansen |
| 6,949,081 B1 | 9/2005 | Chance |
| 6,950,708 B2 | 9/2005 | Bowman et al. |
| 6,951,165 B2 | 10/2005 | Kuhn et al. |
| 6,951,553 B2 | 10/2005 | Bubb et al. |
| 6,952,604 B2 | 10/2005 | DeNuzzio et al. |
| 6,952,963 B2 | 10/2005 | Delnevo |
| 6,955,819 B2 | 10/2005 | Zhang et al. |
| 6,955,915 B2 | 10/2005 | Fodor et al. |
| 6,956,204 B2 | 10/2005 | Dong et al. |
| 6,957,655 B2 | 10/2005 | Erickson et al. |
| 6,957,924 B1 | 10/2005 | McMeekin et al. |
| 6,958,073 B2 | 10/2005 | Rogers et al. |
| 6,958,705 B2 | 10/2005 | Lebel et al. |
| 6,960,184 B2 | 11/2005 | Willis et al. |
| 6,960,192 B1 | 11/2005 | Flaherty et al. |
| 6,962,103 B2 | 11/2005 | Sandlin |
| 6,962,151 B1 | 11/2005 | Knoch et al. |
| 6,963,770 B2 | 11/2005 | Scarantino et al. |
| 6,966,325 B2 | 11/2005 | Erickson |
| 6,969,369 B2 | 11/2005 | Struble |
| 6,970,741 B1 | 11/2005 | Whitehurst et al. |
| 6,970,742 B2 | 11/2005 | Mann et al. |
| 6,971,999 B2 | 12/2005 | Py et al. |
| 6,974,055 B2 | 12/2005 | Moore et al. |
| 6,974,115 B2 | 12/2005 | Silva |
| 6,974,437 B2 | 12/2005 | Lebel et al. |
| 6,974,588 B1 | 12/2005 | Miranda et al. |
| 6,979,308 B1 | 12/2005 | MacDonald et al. |
| 6,979,316 B1 | 12/2005 | Rubin et al. |
| 6,979,326 B2 | 12/2005 | Mann et al. |
| 6,980,855 B2 | 12/2005 | Cho |
| 6,981,499 B2 | 1/2006 | Anderson et al. |
| 6,981,967 B2 | 1/2006 | Massengale et al. |
| 6,982,248 B2 | 1/2006 | Coolidge et al. |
| 6,983,209 B2 | 1/2006 | Jaynes |
| 6,985,770 B2 | 1/2006 | Nyhart |
| 6,985,771 B2 | 1/2006 | Fishell et al. |
| 6,986,867 B2 | 1/2006 | Hanley et al. |

(56) References Cited

U.S. PATENT DOCUMENTS

| | | |
|---|---|---|
| 6,987,129 B2 | 1/2006 | Mak et al. |
| 6,990,809 B2 | 1/2006 | Abouraphael |
| 6,991,619 B2 | 1/2006 | Marano-Ford et al. |
| 6,991,620 B2 | 1/2006 | Marano-Ford et al. |
| 6,993,795 B2 | 2/2006 | Prineppi |
| 6,994,700 B2 | 2/2006 | Elkins et al. |
| 6,997,202 B2 | 2/2006 | Olander |
| 6,997,911 B2 | 2/2006 | Klitmose |
| 6,997,920 B2 | 2/2006 | Mann et al. |
| 6,998,387 B1 | 2/2006 | Goke et al. |
| 6,998,404 B2 | 2/2006 | Moskowitz |
| 6,999,854 B2 | 2/2006 | Roth |
| 7,004,928 B2 | 2/2006 | Aceti et al. |
| 7,008,399 B2 | 3/2006 | Larson et al. |
| 7,008,403 B1 * | 3/2006 | Mallett ................ 604/132 |
| 7,010,340 B2 | 3/2006 | Scarantino et al. |
| 7,011,647 B2 | 3/2006 | Purdy et al. |
| 7,011,682 B2 | 3/2006 | Lashinski et al. |
| 7,013,727 B2 | 3/2006 | Delnevo |
| 7,015,782 B2 | 3/2006 | Kincaid et al. |
| 7,018,360 B2 | 3/2006 | Flaherty et al. |
| 7,018,361 B2 | 3/2006 | Gillespie, Jr. et al. |
| 7,018,630 B2 | 3/2006 | Takaoka |
| 7,022,071 B2 | 4/2006 | Schaupp et al. |
| 7,022,072 B2 | 4/2006 | Fox et al. |
| 7,022,087 B2 | 4/2006 | Dempster et al. |
| 7,022,108 B2 | 4/2006 | Marano-Ford et al. |
| 7,024,244 B2 | 4/2006 | Muhlenberg et al. |
| 7,024,245 B2 | 4/2006 | Lebel et al. |
| 7,025,716 B1 | 4/2006 | Meloul et al. |
| 7,025,743 B2 | 4/2006 | Mann et al. |
| 7,027,478 B2 | 4/2006 | Ackley |
| 7,029,455 B2 | 4/2006 | Flaherty |
| 7,033,843 B2 | 4/2006 | Hasegawa et al. |
| 7,047,070 B2 | 5/2006 | Wilkinson et al. |
| 7,048,193 B2 | 5/2006 | Tsukada et al. |
| 7,048,951 B1 | 5/2006 | Seitz et al. |
| 7,052,251 B2 | 5/2006 | Nason et al. |
| 7,053,761 B2 | 5/2006 | Schofield et al. |
| 7,056,179 B2 | 6/2006 | Courtney |
| 7,056,302 B2 | 6/2006 | Douglas |
| 7,056,494 B2 | 6/2006 | Adjei et al. |
| 7,056,887 B2 | 6/2006 | Coolidge et al. |
| 7,058,438 B2 | 6/2006 | Grace et al. |
| 7,059,348 B2 | 6/2006 | Nat |
| 7,060,856 B2 | 6/2006 | Macikenas et al. |
| 7,064,472 B2 | 6/2006 | Pelrine et al. |
| 7,066,359 B2 | 6/2006 | Greiner-Perth |
| 7,066,910 B2 | 6/2006 | Bauhahn et al. |
| 7,066,915 B2 | 6/2006 | Olsen |
| 7,066,922 B2 | 6/2006 | Angel et al. |
| 7,069,075 B2 | 6/2006 | Olson |
| 7,070,577 B1 | 7/2006 | Haller et al. |
| 7,072,802 B2 | 7/2006 | Hartlaub |
| 7,073,485 B2 | 7/2006 | Truscott et al. |
| 7,073,713 B2 | 7/2006 | Silverbrook et al. |
| 7,074,200 B1 | 7/2006 | Lewis |
| 7,077,822 B1 | 7/2006 | Howard, III |
| 7,078,163 B2 | 7/2006 | Torrianni |
| 7,081,105 B2 | 7/2006 | Reilly et al. |
| 7,082,812 B2 | 8/2006 | Lenormand et al. |
| 7,083,108 B2 | 8/2006 | Silverbrook et al. |
| 7,083,592 B2 | 8/2006 | Lastovich et al. |
| 7,083,599 B2 | 8/2006 | Alchas et al. |
| 7,089,608 B2 | 8/2006 | Erb |
| 7,090,648 B2 | 8/2006 | Sackner et al. |
| 7,091,179 B2 | 8/2006 | Franco |
| 7,092,011 B2 | 8/2006 | Silverbrook et al. |
| 7,095,210 B2 | 8/2006 | Tamura et al. |
| 7,096,889 B1 | 8/2006 | Roys |
| 7,097,104 B2 | 8/2006 | Silverbrook et al. |
| 7,098,803 B2 | 8/2006 | Mann et al. |
| 7,104,973 B2 | 9/2006 | Woolston et al. |
| 7,104,981 B2 | 9/2006 | Elkins et al. |
| 7,107,706 B1 | 9/2006 | Bailey, Sr. et al. |
| 7,108,491 B2 | 9/2006 | Ganser |
| 7,108,679 B2 | 9/2006 | Alchas |
| 7,109,878 B2 | 9/2006 | Mann et al. |
| 7,111,346 B2 | 9/2006 | Inman et al. |
| 7,115,108 B2 | 10/2006 | Wilkinson et al. |
| 7,118,351 B2 | 10/2006 | Effenhauser et al. |
| 7,118,676 B2 | 10/2006 | Mueth et al. |
| 7,122,151 B2 | 10/2006 | Reeder et al. |
| 7,127,292 B2 | 10/2006 | Warman et al. |
| 7,128,727 B2 | 10/2006 | Flaherty et al. |
| 7,128,730 B2 | 10/2006 | Marano-Ford et al. |
| 7,133,329 B2 | 11/2006 | Skyggebjerg et al. |
| 7,136,701 B2 | 11/2006 | Greatbatch et al. |
| 7,137,951 B2 | 11/2006 | Pilarski |
| 7,137,964 B2 | 11/2006 | Flaherty et al. |
| 7,138,141 B2 | 11/2006 | Platz et al. |
| 7,140,332 B2 | 11/2006 | Klein et al. |
| 7,141,425 B2 | 11/2006 | Dzekunov et al. |
| 7,141,812 B2 | 11/2006 | Appleby et al. |
| 7,144,384 B2 | 12/2006 | Gorman et al. |
| 7,144,729 B2 | 12/2006 | Rolland et al. |
| 7,147,386 B2 | 12/2006 | Zhang et al. |
| 7,147,839 B2 | 12/2006 | Sampath et al. |
| 7,150,409 B2 | 12/2006 | Gonneli et al. |
| 7,150,726 B2 | 12/2006 | Dalton |
| 7,150,737 B2 | 12/2006 | Purdy et al. |
| 7,150,741 B2 | 12/2006 | Erickson et al. |
| 7,152,673 B2 | 12/2006 | Lohbeck |
| 7,153,286 B2 | 12/2006 | Busby et al. |
| 7,153,823 B2 | 12/2006 | Franco |
| 7,156,808 B2 | 1/2007 | Quy |
| 7,156,838 B2 | 1/2007 | Gabel et al. |
| 7,159,271 B2 | 1/2007 | Sepke et al. |
| 7,162,303 B2 | 1/2007 | Levin et al. |
| 7,163,385 B2 | 1/2007 | Gharib et al. |
| 7,163,520 B2 | 1/2007 | Bernard et al. |
| 7,166,280 B2 | 1/2007 | Franco |
| 7,187,404 B2 | 3/2007 | Silverbrook et al. |
| 7,187,528 B2 | 3/2007 | Talbot et al. |
| 7,187,969 B2 | 3/2007 | Willis |
| 7,189,352 B2 | 3/2007 | Carpenter et al. |
| 7,193,521 B2 | 3/2007 | Moberg et al. |
| 7,194,890 B2 | 3/2007 | Tanaka et al. |
| 7,195,616 B2 | 3/2007 | Diller et al. |
| 7,198,603 B2 | 4/2007 | Penner et al. |
| 7,198,637 B2 | 4/2007 | Deshmukh et al. |
| 7,198,751 B2 | 4/2007 | Carpenter et al. |
| 7,198,940 B2 | 4/2007 | Vellinger et al. |
| 7,201,319 B2 | 4/2007 | Silverbrook et al. |
| 7,201,730 B2 | 4/2007 | Davidner et al. |
| 7,204,823 B2 | 4/2007 | Estes et al. |
| 7,204,958 B2 | 4/2007 | Olsen et al. |
| 7,207,952 B2 | 4/2007 | Takinami et al. |
| 7,207,964 B2 | 4/2007 | Davidner et al. |
| 7,208,120 B2 | 4/2007 | Bitensky et al. |
| 7,214,207 B2 | 5/2007 | Lynch et al. |
| 7,214,221 B2 | 5/2007 | Fentress et al. |
| 7,214,658 B2 | 5/2007 | Tobinick |
| 7,217,699 B2 | 5/2007 | Yakubov |
| 7,217,796 B2 | 5/2007 | Wang et al. |
| 7,220,109 B2 | 5/2007 | Kultgen |
| 7,220,236 B2 | 5/2007 | Pan |
| 7,220,248 B2 | 5/2007 | Mernoe et al. |
| 7,220,365 B2 | 5/2007 | Qu et al. |
| 7,225,807 B2 | 6/2007 | Papania et al. |
| 7,226,278 B2 | 6/2007 | Nason et al. |
| 7,226,910 B2 | 6/2007 | Wilson et al. |
| 7,229,288 B2 | 6/2007 | Stuart et al. |
| 7,231,263 B2 | 6/2007 | Choi |
| 7,232,423 B2 | 6/2007 | Mernoe et al. |
| 7,232,430 B2 | 6/2007 | Carlisle et al. |
| 7,232,435 B2 | 6/2007 | Hildebrand et al. |
| 7,234,645 B2 | 6/2007 | Silverbrook |
| 7,235,164 B2 | 6/2007 | Anex et al. |
| 7,235,583 B1 | 6/2007 | Webb et al. |
| 7,237,694 B2 | 7/2007 | Freudinger |
| 7,238,165 B2 | 7/2007 | Vincent et al. |
| 7,239,941 B2 | 7/2007 | Möri et al. |
| 7,244,225 B2 | 7/2007 | Loeb et al. |

(56) References Cited

U.S. PATENT DOCUMENTS

| | | | |
|---|---|---|---|
| 7,244,354 B2 | 7/2007 | Burris et al. |
| 7,247,428 B2 | 7/2007 | Makrigiorgos |
| 7,247,702 B2 | 7/2007 | Gardner et al. |
| 7,250,037 B2 | 7/2007 | Shermer et al. |
| 7,251,516 B2 | 7/2007 | Walker et al. |
| 7,252,014 B1 | 8/2007 | Mayer et al. |
| 7,252,651 B2 | 8/2007 | Haider et al. |
| 7,256,824 B2 | 8/2007 | Silverbrook et al. |
| 7,258,864 B2 | 8/2007 | Clark |
| RE39,816 E | 9/2007 | Stanton et al. |
| 7,264,730 B2 | 9/2007 | Connell et al. |
| 7,265,091 B2 | 9/2007 | Lue et al. |
| 7,267,665 B2 | 9/2007 | Steil et al. |
| 7,267,753 B2 | 9/2007 | Anex et al. |
| 7,267,771 B2 | 9/2007 | Gorsuch et al. |
| 7,268,859 B2 | 9/2007 | Sage, Jr. et al. |
| 7,272,544 B2 | 9/2007 | Gopal et al. |
| 7,276,027 B2 | 10/2007 | Haar et al. |
| 7,276,057 B2 | 10/2007 | Gerber |
| 7,278,983 B2 | 10/2007 | Ireland et al. |
| 7,281,519 B2 | 10/2007 | Schroeder et al. |
| 7,285,293 B2 | 10/2007 | Castillo et al. |
| 7,287,289 B1 | 10/2007 | Hagopian |
| 7,287,485 B2 | 10/2007 | Petrakis |
| 7,288,760 B2 | 10/2007 | Weitz |
| 7,289,142 B2 | 10/2007 | Silverbrook |
| 7,291,126 B2 | 11/2007 | Shekalim et al. |
| 7,291,133 B1 | 11/2007 | Kindler et al. |
| 7,297,151 B2 | 11/2007 | Boecker et al. |
| 7,302,295 B2 | 11/2007 | Stahmann et al. |
| 7,303,543 B1 | 12/2007 | Maule et al. |
| 7,303,549 B2 | 12/2007 | Flaherty et al. |
| 7,303,680 B2 | 12/2007 | Connell et al. |
| 7,304,033 B2 | 12/2007 | Larsen et al. |
| 7,305,975 B2 | 12/2007 | Reddy |
| 7,306,555 B2 | 12/2007 | Dolecek et al. |
| 7,306,578 B2 | 12/2007 | Gray et al. |
| 7,311,693 B2 | 12/2007 | Shekalim et al. |
| 7,316,700 B2 | 1/2008 | Alden et al. |
| 7,316,899 B2 | 1/2008 | McDevitt et al. |
| 7,318,892 B2 | 1/2008 | Connell et al. |
| 7,320,675 B2 | 1/2008 | Pastore et al. |
| 7,320,677 B2 | 1/2008 | Brouillette et al. |
| 7,322,321 B2 | 1/2008 | Robinson |
| 7,323,141 B2 | 1/2008 | Kirchhevel |
| 7,323,543 B2 | 1/2008 | Van Antwerp et al. |
| 7,324,012 B2 | 1/2008 | Mann et al. |
| 7,334,556 B2 | 2/2008 | Wachigai et al. |
| 7,335,377 B2 | 2/2008 | Stern et al. |
| 7,338,464 B2 | 3/2008 | Blischak et al. |
| 7,341,577 B2 | 3/2008 | Gill |
| 7,341,581 B2 | 3/2008 | Mallett |
| 7,344,500 B2 | 3/2008 | Talbot et al. |
| 7,344,507 B2 | 3/2008 | Briggs et al. |
| 7,344,894 B2 | 3/2008 | Greenstein et al. |
| 7,347,201 B2 | 3/2008 | Djupesland |
| 7,347,836 B2 | 3/2008 | Peterson et al. |
| 7,348,176 B2 | 3/2008 | DiMilla et al. |
| 7,351,239 B2 | 4/2008 | Gill |
| 7,351,340 B2 | 4/2008 | Connell et al. |
| 7,351,411 B2 | 4/2008 | Holash et al. |
| 7,351,695 B2 | 4/2008 | Almarssoo et al. |
| 7,357,794 B2 | 4/2008 | Makower et al. |
| 7,357,899 B2 | 4/2008 | Gaillard et al. |
| 7,358,091 B2 | 4/2008 | Phillips et al. |
| 7,361,155 B2 | 4/2008 | Sage, Jr. et al. |
| 7,362,971 B2 | 4/2008 | Silverbrook et al. |
| 7,363,072 B2 | 4/2008 | Movahed |
| 7,363,075 B2 | 4/2008 | Stern et al. |
| 7,364,566 B2 | 4/2008 | Elkins et al. |
| 7,364,568 B2 | 4/2008 | Angel et al. |
| 7,366,925 B2 | 4/2008 | Keely et al. |
| 7,368,003 B2 | 5/2008 | Crapser et al. |
| 7,371,418 B2 | 5/2008 | Sheabar et al. |
| 7,373,083 B2 | 5/2008 | Silverbrook et al. |
| 7,373,690 B2 | 5/2008 | Sepke et al. |
| 7,374,544 B2 | 5/2008 | Freeman et al. |
| 7,374,556 B2 | 5/2008 | Mallett |
| 7,377,706 B2 | 5/2008 | Silverbrook et al. |
| 7,377,907 B2 | 5/2008 | Shekalim et al. |
| 7,378,270 B2 | 5/2008 | Azarnia et al. |
| 7,378,443 B2 | 5/2008 | Berge |
| 7,380,447 B2 | 6/2008 | Rollinger et al. |
| 7,384,413 B2 | 6/2008 | Gross et al. |
| 7,384,912 B2 | 6/2008 | Stewart |
| 7,385,443 B1 | 6/2008 | Denison |
| 7,386,346 B2 | 6/2008 | Struble |
| 7,390,311 B2 | 6/2008 | Hildebrand et al. |
| 7,390,458 B2 | 6/2008 | Burow et al. |
| 7,394,182 B2 | 7/2008 | Pelrine et al. |
| 7,399,277 B2 | 7/2008 | Saidara et al. |
| 7,399,304 B2 | 7/2008 | Gambale et al. |
| 7,399,401 B2 | 7/2008 | Rush |
| 7,399,772 B2 | 7/2008 | Phillips |
| 7,402,153 B2 | 7/2008 | Steil et al. |
| 7,402,154 B2 | 7/2008 | Holst et al. |
| 7,407,489 B2 | 8/2008 | Holst et al. |
| 7,407,490 B2 | 8/2008 | Bendsen et al. |
| 7,410,468 B2 | 8/2008 | Freeman et al. |
| 7,411,204 B2 | 8/2008 | Appleby et al. |
| 7,416,644 B2 | 8/2008 | Bonde |
| 7,421,316 B2 | 9/2008 | Gray et al. |
| 7,421,882 B2 | 9/2008 | Leddy et al. |
| 7,425,204 B2 | 9/2008 | Angel et al. |
| 7,426,408 B2 | 9/2008 | DeNuzzio et al. |
| 7,429,255 B2 | 9/2008 | Thompson |
| 7,429,258 B2 | 9/2008 | Angel et al. |
| 7,429,269 B2 | 9/2008 | Schwammenthal et al. |
| 7,435,250 B2 | 10/2008 | Francischelli et al. |
| 7,435,717 B2 | 10/2008 | Bisgaier et al. |
| 7,440,806 B1 | 10/2008 | Whitehurst et al. |
| 7,442,186 B2 | 10/2008 | Blomquist |
| 7,442,682 B2 | 10/2008 | Kitaura et al. |
| RE40,570 E | 11/2008 | Carpentier et al. |
| 7,445,616 B2 | 11/2008 | Petrakis |
| 7,446,091 B2 | 11/2008 | Van Den Berghe |
| 7,449,333 B2 | 11/2008 | Rolland et al. |
| 7,452,301 B2 | 11/2008 | Yoshioka |
| 7,455,835 B2 | 11/2008 | Cohen et al. |
| 7,459,305 B2 | 12/2008 | Levy |
| 7,460,152 B2 | 12/2008 | Silverbrook et al. |
| 7,460,350 B2 | 12/2008 | Talbot et al. |
| 7,460,895 B2 | 12/2008 | Arnold et al. |
| 7,462,166 B2 | 12/2008 | Cowan |
| 7,463,934 B2 | 12/2008 | Tronnes et al. |
| 7,464,580 B2 | 12/2008 | Zeng et al. |
| 7,464,704 B2 | 12/2008 | Braithwaite |
| 7,465,285 B2 | 12/2008 | Hutchinson et al. |
| 7,465,375 B2 | 12/2008 | Demers et al. |
| 7,467,027 B2 | 12/2008 | Ding et al. |
| 7,467,613 B2 | 12/2008 | Taylor, Sr. |
| 7,469,697 B2 | 12/2008 | Lee et al. |
| 7,469,844 B2 | 12/2008 | Conway et al. |
| 7,470,246 B2 | 12/2008 | Mori et al. |
| 7,473,247 B2 | 1/2009 | Mikszta et al. |
| 7,474,968 B2 | 1/2009 | Ding et al. |
| 7,475,825 B2 | 1/2009 | Silverbrook et al. |
| 7,476,200 B2 | 1/2009 | Tal |
| 7,476,209 B2 | 1/2009 | Gara et al. |
| 7,479,123 B2 | 1/2009 | Briggs |
| 7,481,218 B2 | 1/2009 | Djupesland |
| 7,481,759 B2 | 1/2009 | Whitehurst et al. |
| 7,481,776 B2 | 1/2009 | Boecker et al. |
| 7,481,792 B2 | 1/2009 | Gonelli et al. |
| 7,483,050 B2 | 1/2009 | Silverbrook et al. |
| 7,483,743 B2 | 1/2009 | Mann et al. |
| 7,485,298 B2 | 2/2009 | Powell |
| 7,491,178 B2 | 2/2009 | Boecker et al. |
| 7,491,187 B2 | 2/2009 | Van Den Berghe et al. |
| 7,491,335 B2 | 2/2009 | Reddy et al. |
| 7,493,154 B2 | 2/2009 | Bonner et al. |
| 7,493,171 B1 | 2/2009 | Whitehurst et al. |
| 7,497,841 B2 | 3/2009 | Alchas |
| 7,503,903 B2 | 3/2009 | Carlisle et al. |

(56) References Cited

U.S. PATENT DOCUMENTS

| | | |
|---|---|---|
| 7,505,869 B2 | 3/2009 | Hartlaub |
| 7,507,220 B2 | 3/2009 | Childers et al. |
| 7,507,235 B2 | 3/2009 | Keogh et al. |
| 7,509,169 B2 | 3/2009 | Eigler et al. |
| 7,511,914 B2 | 3/2009 | Hiller et al. |
| 7,514,075 B2 | 4/2009 | Hedrick et al. |
| 7,514,401 B2 | 4/2009 | Franco |
| 7,515,060 B2 | 4/2009 | Blomquist |
| 7,517,335 B2 | 4/2009 | Gravesen et al. |
| 7,517,440 B2 | 4/2009 | Anex et al. |
| 7,517,498 B2 | 4/2009 | Fredrick |
| 7,517,530 B2 | 4/2009 | Clark |
| 7,524,045 B2 | 4/2009 | Silverbrook et al. |
| 7,524,287 B2 | 4/2009 | Bharmi |
| 7,524,293 B2 | 4/2009 | Freeman et al. |
| 7,524,304 B2 | 4/2009 | Genosar |
| 7,530,968 B2 | 5/2009 | Gonnelli |
| 7,530,975 B2 | 5/2009 | Hunter |
| 7,534,221 B2 | 5/2009 | Pile-Spellman |
| 7,534,226 B2 | 5/2009 | Mernoe et al. |
| 7,536,983 B2 | 5/2009 | Layher et al. |
| 7,537,571 B2 | 5/2009 | Freeman et al. |
| 7,540,859 B2 | 6/2009 | Claude et al. |
| 7,540,880 B2 | 6/2009 | Nolting |
| 7,543,581 B2 | 6/2009 | Djupesland |
| 7,547,287 B2 | 6/2009 | Boecker et al. |
| 7,548,314 B2 | 6/2009 | Altobelli et al. |
| 7,551,202 B2 | 6/2009 | Silverbrook |
| 7,553,813 B2 | 6/2009 | Unemori |
| 7,556,613 B2 | 7/2009 | Wittmann et al. |
| 7,556,841 B2 | 7/2009 | Kimball et al. |
| 7,558,629 B2 | 7/2009 | Keimel et al. |
| 7,559,223 B2 | 7/2009 | Chen et al. |
| 7,559,524 B2 | 7/2009 | Gray et al. |
| 7,563,232 B2 | 7/2009 | Freeman et al. |
| 7,563,255 B2 | 7/2009 | Adamis et al. |
| D598,109 S | 8/2009 | Collins et al. |
| 7,571,635 B2 | 8/2009 | Lyon |
| 7,572,789 B2 | 8/2009 | Cowen et al. |
| 7,577,477 B2 | 8/2009 | Allen et al. |
| 7,582,063 B2 | 9/2009 | Wurster et al. |
| 7,582,099 B2 | 9/2009 | Freeman et al. |
| 7,584,846 B2 | 9/2009 | Senter |
| 7,588,046 B1 | 9/2009 | Erickson |
| 7,588,550 B2 | 9/2009 | Leonard et al. |
| 7,588,784 B2 | 9/2009 | Maday et al. |
| 7,589,059 B2 | 9/2009 | Wolff et al. |
| 7,590,443 B2 | 9/2009 | Bharmi |
| 7,591,801 B2 | 9/2009 | Brauker et al. |
| 7,594,889 B2 | 9/2009 | St. Ores et al. |
| 7,598,031 B2 | 10/2009 | Liew |
| 7,602,310 B2 | 10/2009 | Mann et al. |
| 7,603,174 B2 | 10/2009 | De Ridder |
| 7,604,592 B2 | 10/2009 | Freeman et al. |
| 7,604,593 B2 | 10/2009 | Parris et al. |
| 7,604,619 B2 | 10/2009 | Eich et al. |
| 7,605,710 B2 | 10/2009 | Crnkovich et al. |
| 7,606,274 B2 | 10/2009 | Mirov et al. |
| 7,606,615 B2 | 10/2009 | Makower et al. |
| 7,607,965 B1 | 10/2009 | Frazier |
| 7,608,640 B2 | 10/2009 | Messadek |
| 7,615,046 B2 | 11/2009 | Shehata |
| 7,618,615 B2 | 11/2009 | Frey, II et al. |
| 7,618,954 B2 | 11/2009 | Nicolau et al. |
| 7,624,409 B2 | 11/2009 | Whymark |
| 7,625,354 B2 | 12/2009 | Hochman |
| 7,625,369 B2 | 12/2009 | Abboud et al. |
| 7,628,590 B2 | 12/2009 | Jacobsen et al. |
| 7,628,772 B2 | 12/2009 | McConnell et al. |
| 7,632,228 B2 | 12/2009 | Brauker et al. |
| 7,632,247 B2 | 12/2009 | Adams |
| 7,632,248 B2 | 12/2009 | Delk et al. |
| 7,635,575 B2 | 12/2009 | Scherze et al. |
| 7,637,931 B2 | 12/2009 | Heaton |
| 7,638,095 B2 | 12/2009 | Sabol |
| 7,642,232 B2 | 1/2010 | Green et al. |
| 7,644,203 B2 | 1/2010 | Ingles |
| 7,645,253 B2 | 1/2010 | Gura et al. |
| 7,647,107 B2 | 1/2010 | Warman et al. |
| 7,647,115 B2 | 1/2010 | Levin et al. |
| 7,647,237 B2 | 1/2010 | Malave et al. |
| 7,650,181 B2 | 1/2010 | Freeman et al. |
| 7,650,190 B2 | 1/2010 | Zhou et al. |
| 7,651,489 B2 | 1/2010 | Estes et al. |
| 7,651,868 B2 | 1/2010 | McDevitt et al. |
| 7,653,639 B2 | 1/2010 | Classen |
| 7,654,127 B2 | 2/2010 | Krulevitch et al. |
| 7,654,131 B2 | 2/2010 | Ascheman |
| 7,654,484 B2 | 2/2010 | Mogensen et al. |
| 7,654,976 B2 | 2/2010 | Peterson et al. |
| 7,654,982 B2 | 2/2010 | Carlisle et al. |
| 7,655,221 B2 | 2/2010 | Rasmussen et al. |
| 7,657,313 B2 | 2/2010 | Rom |
| 7,662,105 B2 | 2/2010 | Hatlestad |
| 7,662,140 B2 | 2/2010 | Heruth et al. |
| 7,662,558 B2 | 2/2010 | Liew |
| 7,674,243 B2 | 3/2010 | Dacquay et al. |
| 7,674,485 B2 | 3/2010 | Bhaskaran et al. |
| 7,676,263 B2 | 3/2010 | Harris et al. |
| 7,678,071 B2 | 3/2010 | Lebel et al. |
| 7,678,761 B2 | 3/2010 | Coleman |
| 7,678,762 B2 | 3/2010 | Green et al. |
| 7,678,763 B2 | 3/2010 | Green et al. |
| 7,678,772 B2 | 3/2010 | Jia et al. |
| 7,678,833 B2 | 3/2010 | Ott |
| 7,682,430 B2 | 3/2010 | Kraemer et al. |
| 7,682,563 B2 | 3/2010 | Carpenter et al. |
| 7,683,029 B2 | 3/2010 | Hindle et al. |
| 7,685,865 B2 | 3/2010 | Norenberg |
| 7,687,272 B1 | 3/2010 | Buchwald et al. |
| RE41,288 E | 4/2010 | Coolidge et al. |
| D613,411 S | 4/2010 | Collins et al. |
| 7,691,330 B1 | 4/2010 | Winkler et al. |
| 7,695,627 B2 | 4/2010 | Bosch et al. |
| 7,697,995 B2 | 4/2010 | Cross, Jr. et al. |
| 7,699,767 B2 | 4/2010 | Mueth et al. |
| 7,699,833 B2 | 4/2010 | Moberg et al. |
| 7,704,226 B2 | 4/2010 | Mueller, Jr. et al. |
| 7,704,227 B2 | 4/2010 | Moberg et al. |
| 7,708,717 B2 | 5/2010 | Estes et al. |
| 7,708,872 B2 | 5/2010 | Eidsned et al. |
| 7,708,915 B2 | 5/2010 | Castor |
| 7,713,240 B2 | 5/2010 | Istoc et al. |
| 7,713,262 B2 | 5/2010 | Adams et al. |
| 7,714,757 B2 | 5/2010 | Denison et al. |
| 7,714,889 B2 | 5/2010 | Silverbrook |
| 7,715,917 B2 | 5/2010 | Chinchoy et al. |
| 7,716,964 B2 | 5/2010 | Kurtz et al. |
| 7,717,856 B2 | 5/2010 | Chen et al. |
| 7,717,871 B2 | 5/2010 | Odland |
| 7,717,903 B2 | 5/2010 | Estes et al. |
| 7,726,955 B2 | 6/2010 | Ryser et al. |
| 7,727,181 B2 | 6/2010 | Rush |
| 7,753,885 B2 | 7/2010 | Duchon et al. |
| 7,771,414 B2 | 8/2010 | Trieu |
| 7,811,279 B2 | 10/2010 | John |
| RE41,956 E | 11/2010 | Klitgaard et al. |
| 7,914,450 B2 | 3/2011 | Goode, Jr. et al. |
| 7,914,499 B2 | 3/2011 | Gonnelli et al. |
| 7,922,096 B2 | 4/2011 | Eilersen |
| 7,931,864 B2 | 4/2011 | Kloepfer et al. |
| 7,935,079 B2 | 5/2011 | Ludin et al. |
| 7,955,305 B2 | 6/2011 | Moberg et al. |
| 7,963,945 B2 | 6/2011 | Miller et al. |
| 7,981,076 B2 | 7/2011 | Sullivan et al. |
| RE42,682 E | 9/2011 | Barreras, Sr. et al. |
| 8,030,058 B1 | 10/2011 | Benedict et al. |
| 8,032,226 B2 | 10/2011 | Miller et al. |
| 8,043,281 B2 | 10/2011 | Heruth et al. |
| RE42,958 E | 11/2011 | Loeb et al. |
| 8,056,582 B2 | 11/2011 | DiPerna |
| 8,062,257 B2 | 11/2011 | Moberg et al. |
| 8,066,629 B2 | 11/2011 | Dlugos |
| 8,094,009 B2 | 1/2012 | Allen et al. |

(56) References Cited

U.S. PATENT DOCUMENTS

| | | | |
|---|---|---|---|
| 8,147,451 B2 | 4/2012 | Brockman et al. | |
| 8,287,495 B2 | 10/2012 | Michaud et al. | |
| 8,292,876 B2 | 10/2012 | Kriesel et al. | |
| 8,298,183 B2 | 10/2012 | Menot et al. | |
| 8,298,184 B2 | 10/2012 | DiPerna et al. | |
| 8,328,754 B2 | 12/2012 | Estes et al. | |
| 8,372,040 B2 | 2/2013 | Huang et al. | |
| 8,408,421 B2 | 4/2013 | DiPerna | |
| 2001/0000282 A1 | 4/2001 | Poleshuk et al. | |
| 2001/0027791 A1 | 10/2001 | Wallace et al. | |
| 2002/0004015 A1 | 1/2002 | Carlisle et al. | |
| 2002/0018720 A1 | 2/2002 | Carlisle et al. | |
| 2002/0019714 A1 | 2/2002 | Carliale et al. | |
| 2002/0040208 A1 | 4/2002 | Flaherty et al. | |
| 2002/0045265 A1 | 4/2002 | Bergh et al. | |
| 2002/0048536 A1 | 4/2002 | Bergh et al. | |
| 2002/0055787 A1 | 5/2002 | Lennox et al. | |
| 2002/0059959 A1 | 5/2002 | Qatu et al. | |
| 2002/0072733 A1 | 6/2002 | Flaherty | |
| 2002/0117214 A1 | 8/2002 | Tucker et al. | |
| 2002/0120234 A1 | 8/2002 | Kong | |
| 2002/0154571 A1 | 10/2002 | Cefai et al. | |
| 2003/0014016 A1 | 1/2003 | Purdy | |
| 2003/0032930 A1 | 2/2003 | Branch et al. | |
| 2003/0036725 A1 | 2/2003 | Lavi et al. | |
| 2003/0055380 A1 | 3/2003 | Flaherty | |
| 2003/0060765 A1 | 3/2003 | Campbell et al. | |
| 2003/0065287 A1 | 4/2003 | Spohn et al. | |
| 2003/0093105 A1 | 5/2003 | Huffmaster | |
| 2003/0097082 A1 | 5/2003 | Purdy et al. | |
| 2003/0130577 A1 | 7/2003 | Purdy et al. | |
| 2003/0183289 A1 | 10/2003 | Seuret et al. | |
| 2003/0212364 A1 | 11/2003 | Mann et al. | |
| 2003/0216683 A1 | 11/2003 | Shekalim | |
| 2004/0010207 A1 | 1/2004 | Flaherty et al. | |
| 2004/0051368 A1 | 3/2004 | Caputo | |
| 2004/0078028 A1 | 4/2004 | Flaherty et al. | |
| 2004/0092865 A1 | 5/2004 | Flaherty et al. | |
| 2004/0116866 A1 | 6/2004 | Gorman et al. | |
| 2004/0116905 A1 | 6/2004 | Pederson et al. | |
| 2004/0122353 A1 | 6/2004 | Shahmirian et al. | |
| 2004/0133220 A1 | 7/2004 | Lashinski et al. | |
| 2004/0138744 A1 | 7/2004 | Lashinski et al. | |
| 2004/0153146 A1 | 8/2004 | Lashinski et al. | |
| 2004/0167478 A1 | 8/2004 | Mooney et al. | |
| 2004/0171987 A1 | 9/2004 | Bridle et al. | |
| 2004/0193090 A1 | 9/2004 | Lebel et al. | |
| 2004/0204673 A1 | 10/2004 | Flaherty | |
| 2004/0220551 A1 | 11/2004 | Flaherty et al. | |
| 2004/0225252 A1 | 11/2004 | Gillespie et al. | |
| 2004/0235446 A1 | 11/2004 | Flaherty et al. | |
| 2004/0260233 A1 | 12/2004 | Garibotto et al. | |
| 2005/0020980 A1 | 1/2005 | Inoue et al. | |
| 2005/0022274 A1 | 1/2005 | Campbell et al. | |
| 2005/0038379 A1 | 2/2005 | Beebe et al. | |
| 2005/0043710 A1 | 2/2005 | Hadzic et al. | |
| 2005/0054994 A1 | 3/2005 | Cioanta et al. | |
| 2005/0060030 A1 | 3/2005 | Lashinski et al. | |
| 2005/0115622 A1 | 6/2005 | Bennett et al. | |
| 2005/0137530 A1 | 6/2005 | Campbell et al. | |
| 2005/0137578 A1 | 6/2005 | Heruth et al. | |
| 2005/0171512 A1 | 8/2005 | Flaherty | |
| 2005/0171513 A1 | 8/2005 | Mann et al. | |
| 2005/0171569 A1 | 8/2005 | Girard et al. | |
| 2005/0182366 A1 | 8/2005 | Vogt et al. | |
| 2005/0211322 A1 | 9/2005 | Lohbeck | |
| 2005/0238507 A1 | 10/2005 | Dilanni et al. | |
| 2005/0240119 A1 | 10/2005 | Draudt et al. | |
| 2005/0245867 A1 | 11/2005 | Olsen et al. | |
| 2006/0041229 A1 | 2/2006 | Garibotto et al. | |
| 2006/0042695 A1 | 3/2006 | Gonia | |
| 2006/0116757 A1 | 6/2006 | Lashinski et al. | |
| 2006/0139354 A1 | 6/2006 | Suma | |
| 2006/0147313 A1 | 7/2006 | Zengerle et al. | |
| 2006/0149214 A1 | 7/2006 | Breiter et al. | |
| 2006/0150747 A1 | 7/2006 | Mallett | |
| 2006/0150748 A1* | 7/2006 | Mallett | 73/861.42 |
| 2006/0178633 A1 | 8/2006 | Garibotto et al. | |
| 2006/0189895 A1 | 8/2006 | Neel et al. | |
| 2006/0206029 A1 | 9/2006 | Yair | |
| 2006/0206054 A1 | 9/2006 | Shekalim et al. | |
| 2006/0229557 A1 | 10/2006 | Fathallah et al. | |
| 2006/0243804 A1 | 11/2006 | Cristoffersen et al. | |
| 2006/0264835 A1 | 11/2006 | Nielson et al. | |
| 2006/0271022 A1 | 11/2006 | Steinbach et al. | |
| 2006/0282290 A1 | 12/2006 | Flaherty et al. | |
| 2007/0000337 A1 | 1/2007 | Gross | |
| 2007/0003434 A1 | 1/2007 | Padmanabhan et al. | |
| 2007/0033074 A1 | 2/2007 | Nitzan et al. | |
| 2007/0100235 A1 | 5/2007 | Kennedy | |
| 2007/0118405 A1 | 5/2007 | Campbell et al. | |
| 2007/0123819 A1 | 5/2007 | Mernoe et al. | |
| 2007/0124002 A1 | 5/2007 | Estes et al. | |
| 2007/0142822 A1 | 6/2007 | Remde | |
| 2007/0149926 A1 | 6/2007 | Moberg et al. | |
| 2007/0150019 A1 | 6/2007 | Youker et al. | |
| 2007/0156092 A1 | 7/2007 | Estes et al. | |
| 2007/0161955 A1 | 7/2007 | Bynum et al. | |
| 2007/0167905 A1 | 7/2007 | Estes et al. | |
| 2007/0167912 A1 | 7/2007 | Causey et al. | |
| 2007/0173762 A1 | 7/2007 | Estes et al. | |
| 2007/0179444 A1 | 8/2007 | Causey et al. | |
| 2007/0201992 A1 | 8/2007 | Mernoe et al. | |
| 2007/0203459 A1 | 8/2007 | Mernoe et al. | |
| 2007/0219496 A1 | 9/2007 | Kamen et al. | |
| 2007/0250007 A1 | 10/2007 | Shekalim | |
| 2007/0264130 A1* | 11/2007 | Mallett | 417/38 |
| 2007/0287985 A1 | 12/2007 | Estes et al. | |
| 2007/0288176 A1 | 12/2007 | Carlisle et al. | |
| 2008/0004601 A1 | 1/2008 | Jennewine et al. | |
| 2008/0015510 A1 | 1/2008 | Sandoz et al. | |
| 2008/0029173 A1 | 2/2008 | DiPerna | |
| 2008/0033357 A1 | 2/2008 | Mann et al. | |
| 2008/0045902 A1 | 2/2008 | Estes et al. | |
| 2008/0045903 A1 | 2/2008 | Estes et al. | |
| 2008/0045904 A1 | 2/2008 | Estes et al. | |
| 2008/0045931 A1 | 2/2008 | Estes et al. | |
| 2008/0051716 A1 | 2/2008 | Stutz | |
| 2008/0065007 A1 | 3/2008 | Peterson et al. | |
| 2008/0065016 A1 | 3/2008 | Peterson et al. | |
| 2008/0071220 A1 | 3/2008 | Rhinehart et al. | |
| 2008/0082040 A1 | 4/2008 | Kubler et al. | |
| 2008/0092969 A1 | 4/2008 | DiPerna | |
| 2008/0097291 A1 | 4/2008 | Hanson et al. | |
| 2008/0097375 A1 | 4/2008 | Bikovsky | |
| 2008/0114228 A1 | 5/2008 | McCloskey et al. | |
| 2008/0116647 A1 | 5/2008 | Anderson et al. | |
| 2008/0147004 A1 | 6/2008 | Mann et al. | |
| 2008/0147050 A1 | 6/2008 | Mann et al. | |
| 2008/0160492 A1 | 7/2008 | Campbell et al. | |
| 2008/0196762 A1 | 8/2008 | Mallett | |
| 2008/0197801 A1 | 8/2008 | Manor et al. | |
| 2008/0234637 A1 | 9/2008 | McConnell et al. | |
| 2008/0281276 A1 | 11/2008 | Shekalim et al. | |
| 2008/0294094 A1 | 11/2008 | Mhatre et al. | |
| 2008/0294108 A1 | 11/2008 | Briones et al. | |
| 2008/0294109 A1 | 11/2008 | Estes et al. | |
| 2008/0294142 A1 | 11/2008 | Patel et al. | |
| 2008/0304365 A1 | 12/2008 | Jarvis et al. | |
| 2009/0026146 A1 | 1/2009 | Carlisle et al. | |
| 2009/0067989 A1 | 3/2009 | Estes et al. | |
| 2009/0069745 A1 | 3/2009 | Estes et al. | |
| 2009/0069746 A1 | 3/2009 | Miller et al. | |
| 2009/0069749 A1 | 3/2009 | Miller et al. | |
| 2009/0069784 A1 | 3/2009 | Estes et al. | |
| 2009/0069785 A1 | 3/2009 | Miller et al. | |
| 2009/0069787 A1 | 3/2009 | Estes et al. | |
| 2009/0088701 A1 | 4/2009 | Larsen | |
| 2009/0131863 A1 | 5/2009 | Carlisle et al. | |
| 2009/0143732 A1 | 6/2009 | O'Connor et al. | |
| 2009/0156990 A1 | 6/2009 | Wenger et al. | |
| 2009/0191067 A1 | 7/2009 | DiPerna | |
| 2009/0192366 A1 | 7/2009 | Mensinger | |
| 2009/0192724 A1 | 7/2009 | Brauker et al. | |

(56) References Cited

U.S. PATENT DOCUMENTS

| | | |
|---|---|---|
| 2009/0192745 A1 | 7/2009 | Kamath |
| 2009/0217982 A1 | 9/2009 | DiPerna |
| 2009/0229374 A1 | 9/2009 | Carlisle et al. |
| 2009/0234594 A1 | 9/2009 | Carlisle et al. |
| 2009/0247982 A1 | 10/2009 | Krulevitch et al. |
| 2009/0254037 A1 | 10/2009 | Bryant et al. |
| 2009/0270833 A1 | 10/2009 | DeBelser et al. |
| 2009/0272928 A1 | 11/2009 | Alvarez et al. |
| 2009/0275887 A1 | 11/2009 | Estes |
| 2009/0287180 A1 | 11/2009 | DiPerna |
| 2009/0292245 A1 | 11/2009 | Basso et al. |
| 2009/0321675 A1 | 12/2009 | Alvarez et al. |
| 2010/0008795 A1 | 1/2010 | Diperna |
| 2010/0032041 A1 | 2/2010 | DiPerna |
| 2010/0036327 A1 | 2/2010 | DiPerna |
| 2010/0038572 A1 | 2/2010 | Alvarez et al. |
| 2010/0043738 A1 | 2/2010 | Grandvallet et al. |
| 2010/0049164 A1 | 2/2010 | Estes et al. |
| 2010/0063765 A1 | 3/2010 | Carlisle et al. |
| 2010/0065578 A1 | 3/2010 | DiPerna |
| 2010/0065579 A1 | 3/2010 | DiPerna |
| 2010/0069890 A1 | 3/2010 | Graskov et al. |
| 2010/0071446 A1 | 3/2010 | Brown |
| 2010/0081993 A1 | 4/2010 | O'Connor |
| 2010/0094114 A1 | 4/2010 | Robinson et al. |
| 2010/0094251 A1 | 4/2010 | Estes et al. |
| 2010/0096019 A1 | 4/2010 | DiPerna |
| 2010/0106100 A1 | 4/2010 | Petersen |
| 2010/0121306 A1 | 5/2010 | Yodfat et al. |
| 2010/0137833 A1 | 6/2010 | Glynn |
| 2010/0145303 A1 | 6/2010 | Yodfat et al. |
| 2010/0165795 A1 | 7/2010 | Elder et al. |
| 2010/0168543 A1 | 7/2010 | Kamath et al. |
| 2010/0168711 A1 | 7/2010 | Bazargan et al. |
| 2010/0179402 A1 | 7/2010 | Goode, Jr. et al. |
| 2010/0198183 A1 | 8/2010 | Lanigan et al. |
| 2010/0218586 A1 | 9/2010 | Rosinko et al. |
| 2010/0228186 A1 | 9/2010 | Estes et al. |
| 2010/0249566 A1 | 9/2010 | Suess et al. |
| 2010/0274515 A1 | 10/2010 | Hoss et al. |
| 2010/0298681 A1 | 11/2010 | Say |
| 2010/0324394 A1 | 12/2010 | Say et al. |
| 2011/0009813 A1 | 1/2011 | Rankers |
| 2011/0028937 A1 | 2/2011 | Powers et al. |
| 2011/0033833 A1 | 2/2011 | Blomquist |
| 2011/0050428 A1 | 3/2011 | Istoc |
| 2011/0056264 A1 | 3/2011 | Kaplan et al. |
| 2011/0108158 A1 | 5/2011 | Huwiler et al. |
| 2011/0111794 A1 | 5/2011 | Bochenko |
| 2011/0120206 A1 | 5/2011 | Troughton et al. |
| 2011/0124996 A1 | 5/2011 | Reinke et al. |
| 2011/0144586 A1 | 6/2011 | Michaud et al. |
| 2011/0144616 A1 | 6/2011 | Michaud et al. |
| 2011/0152769 A1 | 6/2011 | Ramey et al. |
| 2011/0152770 A1 | 6/2011 | DiPerna |
| 2011/0152824 A1 | 6/2011 | DiPerna et al. |
| 2011/0163125 A1 | 7/2011 | Beavis et al. |
| 2011/0166544 A1 | 7/2011 | Verhoef et al. |
| 2012/0029433 A1 | 2/2012 | Michaud et al. |
| 2012/0029468 A1 | 2/2012 | DiPerna et al. |
| 2012/0029486 A1 | 2/2012 | Laerdal et al. |
| 2012/0029708 A1 | 2/2012 | Miller et al. |
| 2012/0030610 A1 | 2/2012 | DiPerna et al. |
| 2013/0053816 A1 | 2/2013 | DiPerna et al. |
| 2013/0306191 A1 | 11/2013 | Metzmaker et al. |
| 2013/0324928 A1 | 12/2013 | Kruse |

FOREIGN PATENT DOCUMENTS

| | | |
|---|---|---|
| CN | 2668847 Y | 1/2005 |
| EP | 0055836 | 7/1982 |
| EP | 0272530 | 6/1988 |
| EP | 0376894 | 12/1988 |
| EP | 0 385 916 A2 | 9/1990 |
| EP | 0494042 | 7/1992 |
| EP | 0560571 | 9/1993 |
| EP | 1217275 | 12/2000 |
| EP | 1938750 | 7/2008 |
| EP | 2416826 | 10/2010 |
| GB | 2159496 | 12/1985 |
| JP | 06-016165 | 4/1994 |
| JP | 08-312820 | 11/1996 |
| JP | 2952037 | 9/1999 |
| JP | 2002-143293 | 5/2002 |
| JP | 2006-009944 | 1/2006 |
| JP | 2006-101985 | 4/2009 |
| JP | 2009-148591 | 7/2009 |
| JP | 2010-075736 | 4/2010 |
| KR | 10-2001-0080519 | 8/2001 |
| WO | 90/13795 | 11/1990 |
| WO | WO 91/00753 | 1/1991 |
| WO | WO 94/26329 | 11/1994 |
| WO | WO 95/32013 | 11/1995 |
| WO | WO 96/08049 | 3/1996 |
| WO | WO9613288 | 5/1996 |
| WO | WO 96/25189 | 8/1996 |
| WO | WO9625189 | 8/1996 |
| WO | WO 98/19627 | 5/1998 |
| WO | 98/57683 | 12/1998 |
| WO | WO 99/01088 | 1/1999 |
| WO | WO 00/10628 | 3/2000 |
| WO | WO 00/35527 | 6/2000 |
| WO | WO 00/40346 | 7/2000 |
| WO | WO 00/72900 | 12/2000 |
| WO | WO0072900 | 12/2000 |
| WO | WO 01/30422 | 5/2001 |
| WO | WO0130422 | 5/2001 |
| WO | 02/11791 | 2/2002 |
| WO | WO 02/11049 | 2/2002 |
| WO | WO 02/26102 | 4/2002 |
| WO | WO 02/28532 | 4/2002 |
| WO | WO 03/081052 | 3/2003 |
| WO | WO 03/102737 | 6/2003 |
| WO | WO 2004/009152 | 1/2004 |
| WO | WO2004009160 | 1/2004 |
| WO | WO 2004/088148 | 3/2004 |
| WO | WO 2004/036150 | 4/2004 |
| WO | WO 2004/047677 | 6/2004 |
| WO | WO 2004/060464 | 7/2004 |
| WO | WO 2004/056412 | 12/2004 |
| WO | WO 2004/105827 | 12/2004 |
| WO | WO 2005/082450 | 2/2005 |
| WO | WO 2005/018507 | 3/2005 |
| WO | WO2005082450 A1 | 9/2005 |
| WO | WO 2006/001024 | 1/2006 |
| WO | WO 2006/108219 | 10/2006 |
| WO | WO 2007/038059 | 4/2007 |
| WO | WO 2007/038060 | 4/2007 |
| WO | WO 2007/038091 | 4/2007 |
| WO | WO 2007/056504 | 5/2007 |
| WO | WO 2007/056592 | 5/2007 |
| WO | WO2007/065944 | 6/2007 |
| WO | WO 2007/089983 | 8/2007 |
| WO | WO 2007/098265 | 8/2007 |
| WO | WO 2007/098287 | 8/2007 |
| WO | WO 2007/106232 | 9/2007 |
| WO | WO 2007/119149 | 10/2007 |
| WO | WO2007119149 | 10/2007 |
| WO | WO2008/024812 | 2/2008 |
| WO | WO 2008/028509 | 3/2008 |
| WO | WO 2008/071220 | 3/2008 |
| WO | WO 2008/037270 | 4/2008 |
| WO | WO 2008/037271 | 4/2008 |
| WO | WO 2008/037272 | 4/2008 |
| WO | WO 2008/037273 | 4/2008 |
| WO | WO 2008/043381 | 4/2008 |
| WO | WO 2008/050126 | 5/2008 |
| WO | WO 2008/050128 | 5/2008 |
| WO | WO 2008/056363 | 5/2008 |
| WO | WO 2008/144693 | 5/2008 |
| WO | WO 2008/144695 | 5/2008 |
| WO | WO 2008/144697 | 5/2008 |
| WO | WO 2008/144698 | 5/2008 |

(56) References Cited

FOREIGN PATENT DOCUMENTS

| | | |
|---|---|---|
| WO | WO 2008/103175 | 8/2008 |
| WO | WO 2008/121599 | 10/2008 |
| WO | WO2009/016636 | 2/2009 |
| WO | WO 2009/106233 | 2/2009 |
| WO | WO 2009/032399 | 3/2009 |
| WO | WO 2009/032400 | 3/2009 |
| WO | WO 2009/032402 | 3/2009 |
| WO | WO 2009/035753 | 3/2009 |
| WO | WO 2009/035759 | 3/2009 |
| WO | WO 2009/035761 | 3/2009 |
| WO | WO 2009/035762 | 3/2009 |
| WO | WO2009044221 | 4/2009 |
| WO | WO 2009/094590 | 7/2009 |
| WO | WO2009094590 A2 | 7/2009 |
| WO | WO 2009/098648 | 8/2009 |
| WO | WO 2009/108639 | 9/2009 |
| WO | WO2009108639 A1 | 9/2009 |
| WO | WO 2009/124133 | 10/2009 |
| WO | WO 2009/143188 | 11/2009 |
| WO | WO 2009/147680 | 12/2009 |
| WO | WO 2010/016977 | 2/2010 |
| WO | WO 2010/016978 | 2/2010 |
| WO | WO 2010/097774 | 2/2010 |
| WO | WO 2010/033634 | 3/2010 |
| WO | WO 2010/033878 | 3/2010 |
| WO | WO 2010/038031 | 4/2010 |
| WO | WO 2010/096449 | 8/2010 |
| WO | WO 2010/099490 | 9/2010 |
| WO | WO 2010/113162 | 10/2010 |
| WO | WO 2011/014704 | 2/2011 |
| WO | WO 2011/017667 | 2/2011 |
| WO | WO2012019726 | 2/2012 |

OTHER PUBLICATIONS

International Search Report and Written Opinion mailed on Sep. 10, 2004 in International Application: PCT/US2003/022703 filed on Jul. 15, 2003 and published as: WO 04/009152 on Jan. 29, 2004.
International Search Report and Written Opinion mailed on: Jul. 23, 2007 in International Application: PCT/2007/060633 filed on: Jan. 17, 2007 and published as: WO 07/089983 on: Aug. 9, 2007.
International Preliminary Report on Patentability mailed on: Jul. 29, 2008 in International Application: PCT/2007/060633 filed on: Jan. 17, 2007 and published as: WO 07/089983 on: Aug. 9, 2007.
International Search Report and Written Opinion mailed on: May 29, 2009 in International Application: PCT/US2009/035022 filed on: Jan. 23, 2009 and published as: WO 09/108639 on: Sep. 3, 2009.
International Preliminary Report on Patentability mailed on: Sep. 10, 2010 in International Application: PCT/US2009/035022 filed on: Jan. 23, 2009 and published as: WO 09/108639 on: Sep. 3, 2009.
International Preliminary Report on Patentability mailed on: Oct. 6, 2009 in International Application: PCT/2008/058044 filed on: Mar. 24, 2008 and published as: WO 08/121599 on: Oct. 9, 2009.
Written Opinion of the International Searching Authority of Aug. 11, 2008 in International Application: PCT/US2008/058044 filed on: Mar. 24, 2008 and published as: WO 08/121599 on: Oct. 9, 2009.
International Search Report and Written Opinion mailed on: Feb. 17, 2011 in International Application: PCT/US2009/049110 filed on: Jun. 29, 2009 and published as: WO 10/016799 on: Feb. 11, 2010.
International Search Report and Written Opinion mailed on: Jan. 27, 2010 in International Application: PCT/US2009/049110 filed on: Jun. 29, 2009 and published as: WO 10/016977 on: Feb. 11, 2010.
International Search Report and Written Opinion mailed on: Feb. 17, 2011 in International Application: PCT/2009/049166 filed on: Jun. 29, 2009 and published as: WO 10/016978 on: Feb. 11, 2010.
International Search Report and Written Opinion mailed on: Feb. 4, 2010 in International Application: PCT/2009/049166 filed on: Jun. 29, 2009 and published as: WO 10/016978 on: Feb. 11, 2010.
International Preliminary Report on Patentability mailed on Aug. 5, 2010 in International Application: PCT/US2009/031906 filed on Jan. 23, 2009 and published as: WO 09/094590 on Jul. 30, 2009.
International Search Report and Written Opinion mailed on Jul. 28, 2009 in International Application: PCT/US2009/031906 filed on Jan. 23, 2009 and published as: WO 09/094590 on Jul. 30, 2009.
International Search Report and Written Opinion mailed on: Apr. 27, 2011 in International Application: PCT/US2010/044789 filed on Aug. 6, 2011 and published as: WO 11/017667 on Feb. 10, 2011.
International Search Report and Written Opinion mailed on: Jan. 4, 2010 in International Application: PCT/US2009/044569 filed on: May 19, 2009 and published as: WO 09/143188 on: Nov. 26, 2009.
International Preliminary Report on Patentability mailed: Dec. 2, 2010, in International Patent Application No. PCT/US2009/044569 filed on: May 19, 2009 and published as WO 2009/143188 on: Nov. 26, 2009.
International Preliminary Report on Patentability mailed on Mar. 31, 2011 in International Application: PCT/2009/057208 filed on: Sep. 16, 2009 and published as: WO 10/033634 on: Mar. 25, 2010.
International Search Report and Written Opinion mailed on Apr. 1, 2010 in International Application: PCT/2009/057208 filed on: Sep. 16, 2009 and published as: WO 10/033634 on: Mar. 25, 2010.
International Search Report and Written Opinion mailed on: Sep. 30, 2010 in International Application: PCT/2010/025663 filed on: Feb. 26, 2010 and published as: WO 10/099490 on: Sep. 2, 2010.
International Preliminary Report on Patentability mailed on Mar. 31, 2011 in International Application: PCT/2009/57591 filed on: Sep. 18, 2009 and published as: WO 10/033878 on: Mar. 25, 2010.
International Search Report and Written Opinion mailed on Apr. 12, 2010 in International Application: PCT/2009/57591 filed on: Sep. 18, 2009 and published as: WO 10/033878 on: Mar. 25, 2010.
International Search Report and Written Opinion mailed on Apr. 11, 2011 in International Application: PCT/2010/043789 filed on: Jul. 29, 2010 and published as: WO 11/014704 on: Feb. 3, 2011.
Office Action mailed on: Dec. 15, 2005 in U.S. Appl. No. 10/200,109, filed May 4, 2007 and issued as: 7,008,403 on: Mar. 7, 2007.
Office Action mailed on: Apr. 14, 2005 in U.S. Appl. No. 10/200,109, filed May 4, 2007 and issued as: 7,008,403 on: Mar. 7, 2007.
Office Action mailed on: Oct. 4, 2004 in U.S. Appl. No. 10/200,109, filed May 4, 2007 and issued as: 7,008,403 on: Mar. 7, 2007.
Office Action mailed on: Jun. 23, 2004 in U.S. Appl. No. 10/200,109, filed May 4, 2007 and issued as: 7,008,403 on: Mar. 7, 2007.
Office Action mailed on: May 29, 2009 in U.S. Appl. No. 11/744,819, filed May 4, 2007 and published as: US-2007-0264130 on Nov. 15, 2007.
Office Action mailed on: Aug. 5, 2009 in U.S. Appl. No. 11/744,819, filed May 4, 2007 and published as: US-2007-0264130 on Nov. 15, 2007.
Office Action mailed on: Mar. 9, 2010 in U.S. Appl. No. 11/744,819, filed May 4, 2007 and published as: US-2007-0264130 on Nov. 15, 2007.
Office Action mailed on: Jan. 8, 2008 in U.S. Appl. No. 11/342,015, filed Jan. 27, 2006 and published as: US-2006-0150747 on: Jul. 13, 2006 and issued as: 7,341,581 on: Mar. 11, 2008.
Office Action mailed on: Jun. 8, 2007 in U.S. Appl. No. 11/343,817, filed Jan. 31, 2006 and published as: US-2006-0150748 on: Jul. 13, 2006 and issued as: 7,374,556 on: May 20, 2008.
Office Action mailed on: Mar. 11, 2008 in U.S. Appl. No. 11/343,817, filed Jan. 31, 2006 and published as: US-2006-0150748 on: Jul. 13, 2006 and issued as: 7,374,556 on: May 20, 2008.
Office Action mailed on: Mar. 3, 2011 in U.S. Appl. No. 12/020,498, filed Jan. 25, 2008 and published as: US-2009-0191067 on: Jul. 30, 2009.
Office Action mailed on: Jul. 18, 2011 in U.S. Appl. No. 12/108,462, filed Apr. 23, 2008 and published as: US-2008-0196762 on: Aug. 21, 2008.
Office Action mailed on: Mar. 21, 2011 in U.S. Appl. No. 12/108,462, filed Apr. 23, 2008 and published as: US-2008-0196762 on: Aug. 21, 2008.
Office Action mailed on: Oct. 6, 2010 in U.S. Appl. No. 12/108,462, filed Apr. 23, 2008 and published as: US-2008-0196762 on: Aug. 21, 2008.
Office Action mailed on Dec. 29, 2009 in U.S. Appl. No. 12/486,795, filed May 19, 2009 and published as US 2009/0287180 on Nov. 19, 2009.

(56) References Cited

OTHER PUBLICATIONS

Office Action mailed on May 27, 2010 in U.S. Appl. No. 12/486,795, filed May 19, 2009 and published as US 2009/0287180 on Nov. 19, 2009.
Office Action mailed on: May 3, 2010 in U.S. Appl. No. 12/189,070, filed Aug. 8, 2008 and published as: US2010/0036327 on Feb. 11, 2010.
Office Action mailed on: Jan. 19, 2011 in U.S. Appl. No. 12/189,070, filed Aug. 8, 2008 and published as: US2010/0036327 on Feb. 11, 2010.
Office Action mailed on: Sep. 6, 2011 in U.S. Appl. No. 12/189,064, filed Aug. 8, 2008 and published as: US2010/0032041 on Feb. 11, 2010.
Office Action mailed on: Jun. 23, 2011 in U.S. Appl. No. 12/189,064, filed Aug. 8, 2008 and published as: US2010/0032041 on Feb. 11, 2010.
Office Action mailed on: Feb. 3, 2011 in U.S. Appl. No. 12/189,064, filed Aug. 8, 2008 and published as: US2010/0032041 on Feb. 11, 2010.
Office Action mailed on: Jul. 1, 2010 in U.S. Appl. No. 12/189,064, filed Aug. 8, 2008 and published as: US2010/0032041 on Feb. 11, 2010.
Office Action mailed on: Jul. 21, 2009 in U.S. Appl. No. 12/189,064, filed Aug. 8, 2008 and published as: US2010/0032041 on Feb. 11, 2010.
Office Action mailed on Aug. 30, 2012 in U.S. Appl. No. 13/273,484, filed Oct. 14, 2011 and published as: US-2012/0030610 on Feb. 2, 2012.
Extended European Search Report mailed on: Mar. 6, 2012 in European Application No. EP 09751416 based on International Application No. PCT/US2009/044569.
Office Action mailed on Mar. 14, 2012 in U.S. Appl. No. 12/260,804, filed Oct. 29, 2008 and published as: US 2010/0065578 on Mar. 18, 2010.
Office Action mailed on Sep. 10, 2012 in U.S. Appl. No. 12/393,973, filed Feb. 26, 2009 and published as: US 2010/0065579 on Mar. 18, 2010.
Office Action mailed on Oct. 24, 2012 in U.S. Appl. No. 12/714,299, filed Feb. 26, 2010 and published as: US 2010/021856 on Sep. 2, 2010.
Office Action mailed on Jul. 12, 2012 in U.S. Appl. No. 13/270,160, filed Oct. 10, 2011 and published as: US 2012/0029433 on Feb. 2, 2012.
Office Action mailed on Apr. 3, 2012 in U.S. Appl. No. 13/270,160, filed Oct. 10, 2011 and published as: US 2012/0029433 on Feb. 2, 2012.
Office Action mailed on Jul. 16, 2012 in U.S. Appl. No. 13/270,156, filed Oct. 11, 2011 and published as: US 2012/0029468 on Feb. 2, 2012.
Office Action mailed on Apr. 2, 2012 in U.S. Appl. No. 13/270,156, filed Oct. 11, 2011 and published as: US 2012/0029468 on Feb. 2, 2012.
Office Action mailed on Nov. 26, 2012 in U.S. Appl. No. 12/846,706, filed Jul. 29, 2010 and published as: US-2011/0144616 on Jun. 16, 2011.
Office Action mailed on Nov. 30, 2012 in U.S. Appl. No. 12/846,733, filed Jul. 29, 2010 and published as: US-2011/0144586 on Jun. 16, 2011.
i-port Advance product brochure, distributed by: Patton Medical Devices and Manufactured by Unomedical, a Cardiovascular Company, Copyright, 2007-2010 Patton Medical Devices, LP.
Arrow International Europe Web Page for: Multiple Lumen Peripheral Catheter, Product No. IV-01150, printed from the internet on Nov. 15, 2011.
AngioDynamics, Smart Port, Power-Injectable Ports Product Brochure, Copyright 2010 AngioDynamics,Inc.
Spring Zone Insulin Delivery System Product Brochure, Copyright 2011 Spring (formerly NiliMEDIX), a D-Medical company.
Miller, John E., "The Reciprocating Pump, Theory, Design and Use," Chapter 1, "Pump Types", Krieger Publishing Company, Malabar, Florida 1995.
Office Action mailed on: Dec. 28, 2011 in U.S. Appl. No. 11/694,841, filed Mar. 30, 2007 and published as: US2008/0029173 on Feb. 7, 2008.
Office Action mailed on: May 5, 2011 in U.S. Appl. No. 11/694,841, filed Mar. 30, 2007 and published as: US2008/0029173 on Feb. 7, 2008.
Office Action mailed on: Jul. 21, 2010 in U.S. Appl. No. 11/694,841, filed Mar. 30, 2007 and published as: US2008/0029173 on Feb. 7, 2008.
Office Action mailed on: Oct. 30, 3009 in U.S. Appl. No. 11/694,841, filed Mar. 30, 2007 and published as: US2008/0029173 on Feb. 7, 2008.
Office Action mailed on: Jun. 24, 2009 in U.S. Appl. No. 11/694,841, filed Mar. 30, 2007 and published as: US2008/0029173 on Feb. 7, 2008.
Office Action mailed on: Sep. 16, 2010 in U.S. Appl. No. 11/462,962, filed Aug. 7, 2006 and published as: US2008/0092969 on Apr. 24, 2008.
Office Action mailed on: Nov. 24, 2009 in U.S. Appl. No. 11/462,962, filed Aug. 7, 2006 and published as: US2008/0092969 on Apr. 24, 2008.
Office Action mailed on: May 5, 2011, in U.S. Appl. No. 12/039,693, filed Feb. 28, 2008 and published as: US2009/0217982 on Sep. 3, 2009.
European Search Report for European Application No. EP10805076 dated Mar. 18, 2013.
European Search Report for European Application No. EP09704892 dated Jan. 28, 2013.
European Search Report for European Application No. EP09751416.0-2319 dated Nov. 21, 2012.
Application and File History of U.S. Appl. No. 12/468,795, filed May 19, 2009, inventor DiPerna.
Application and File History of U.S. Appl. No. 12/020,498, filed Jan. 25, 2008, inventor DiPerna.
Application and File History of U.S. Appl. No. 12/846,688, filed Jul. 29, 2010, inventor DiPerna.
Application and File History of U.S. Appl. No. 12/846,706, filed Jul. 29, 2010, inventor Michaud et al.
Application and File History of U.S. Appl. No. 12/846,720, filed Jul. 29, 2010, inventor DiPerna et al.
Application and File History of U.S. Appl. No. 12/846,733, filed Jul. 29, 2010 inventors Michaud et al.
Application and File History of U.S. Appl. No. 12/846,734, filed Jul. 29, 2010 inventors Verhoef et al.
Application and File History of U.S. Appl. No. 13/270,160, filed Oct. 10, 2011, inventor Michaud et al.
Application and File History of U.S. Appl. No. 13/271,156, filed Oct. 11, 2011, inventors DiPerna et al.
Application and File History of U.S. Appl. No. 13/273,484, filed Oct. 14, 2011, inventors DiPerna et al.
International Search Report and Written Opinion for International Application No. PCT/US2013/044259 dated Sep. 6, 2013.
Examination Report No. 1 for Australian Patent Application No. 2009249132 dated Jan. 23, 2014.

\* cited by examiner

TWO CHAMBER PUMPS AND RELATED METHODS

RELATED APPLICATIONS

This application is a Continuation-in-Part Application and claims the Paris Convention priority of U.S. Utility application Ser. No. 12/020,498, filed Jan. 25, 2008 now abandoned, the content of which are incorporated by reference into this disclosure.

BACKGROUND

The present disclosure relates to the field of pumps, especially those used to accurately dispense medication.

SUMMARY

Two chamber pumps and related methods provide a platform for measuring flow rate in about real time without contacting the material being pumped. Sensors, such as pressure sensors, disposed in a sealed chamber allow for flow material delivery calculations after being calibrated or by knowing the initial volume of the flow material to be delivered. According to a feature of the present disclosure, a device is disclosed comprising a sealed first chamber, which is pressurizable according to embodiments; a second chamber for holding a flow material; at least one flow lumen in flow material communication with the second chamber; at least one sensor disposed in the first chamber; and a flow controller disposed along the flow lumen; and a microprocessor for computing flow rate from data provided by the sensor. A pressurized substance in the first chamber effects a change of volume of the second chamber. The microprocessor controls the flow controller, according to embodiments.

According to a feature of the present disclosure, a device is disclosed comprising a pressurizable first chamber, a second chamber for holding a flow material, at least one flow lumen in flow material communication with the second chamber, at least one pressure sensor disposed in the first chamber, a flow controller disposed along the flow lumen; and a microprocessor to compute at least flow rate of flow material transferred through the at least one flow lumen from the second chamber. A pressurized substance in the first chamber effects a change of volume of the second chamber whereby the fluid flow material flows from the second chamber through the flow lumen. The microprocessor controls the flow controller. According to a feature of the present disclosure, a method is disclosed comprising providing a pump having: (a) a pressurizable first chamber; (b) a second chamber for holding a flow material; (c) at least one sensor disposed in the first chamber; (d) a flow lumen in flow material communication with the second chamber; and (e) a flow controller. A pressurized substance in the first chamber is able to cause the flow material to flow from the second chamber and through the flow restrictor thereby changing the volume of the second chamber.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

In the following detailed description of embodiments of the invention, reference is made to the accompanying drawings in which like references indicate similar elements, and in which is shown by way of illustration specific embodiments in which the invention may be practiced. These embodiments are described in sufficient detail to enable those skilled in the art to practice the invention, and it is to be understood that other embodiments may be utilized and that logical, mechanical, biological, electrical, functional, and other changes may be made without departing from the scope of the present invention. The following detailed description is, therefore, not to be taken in a limiting sense, and the scope of the present invention is defined only by the appended claims. As used in the present disclosure, the term "or" shall be understood to be defined as a logical disjunction and shall not indicate an exclusive disjunction unless expressly indicated as such or notated as "xor."

As used herein, the term "real time" shall be understood to mean the instantaneous moment of an event or condition, or the instantaneous moment of an event or condition plus short period of elapsed time used to make relevant measurements, optional computations, etc., and communicate the measurement, computation, or etc., wherein the state of an event or condition being measured is substantially the same as that of the instantaneous moment irrespective of the elapsed time interval. Used in this context "substantially the same" shall be understood to mean that the data for the event or condition remains useful for the purpose for which it is being gathered after the elapsed time period.

The present disclosure discloses a pump that is able to measure flow rates or adjust flow rates in about real time. The pumps of the present disclosure comprise two chambers with at least a sensor disposed therein to measure the volume in a pressured chamber that drives flow of a flow material from a flow material chamber. A flow material can be a fluid or a gas. Flow controllers are disposed as part of the pump to either prevent flow or regulate and ensure consistent flow rate. The operation of the pumps of the present disclosure maintain sterile conditions for the flow material flow from the pumps, while allowing for precise measurements for flow volumes in about real time without compromising sterility.

Figure 1:
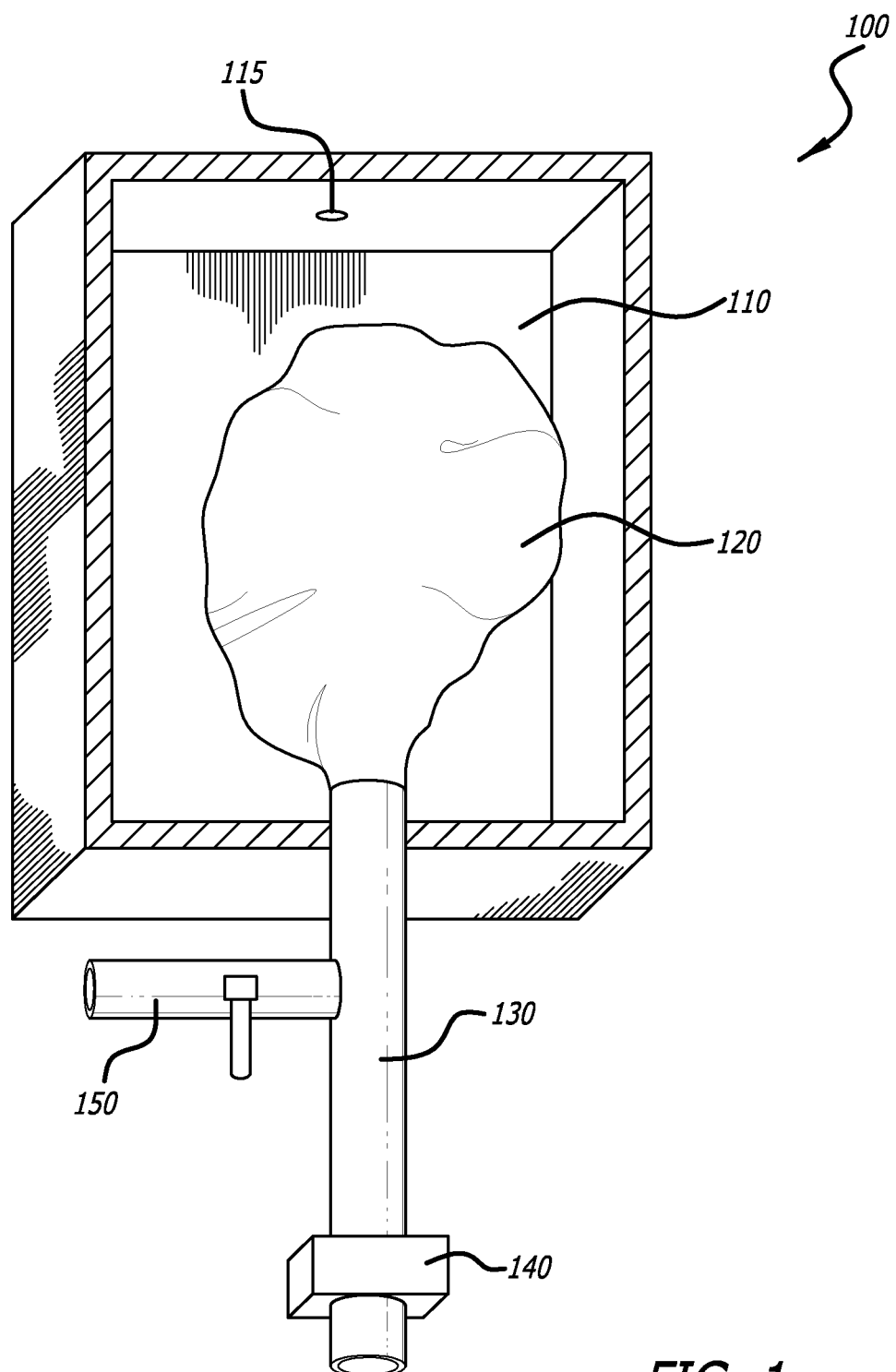
FIG. 1 is a cross sectional view of an embodiment of the pumps of the present disclosure having rigid outer casings.

According to embodiments and as illustrated in FIG. 1, pump 100 comprises first chamber 110 and second chamber 120. First chamber is a chamber that is pressurized such that the pressure in first chamber exceeds the pressure of second chamber. Consequently, when pump 100 is in an flowing state, flow of flow material contained in second chamber 120 is effected.

Flow of flow material from second chamber is through flow lumen 130. Flow lumen may be surgical or medical tubing, pipes, and other similar devices designed for the flow of flow materials from a source to a destination without appreciable loss of flow material.

According to embodiments, flow controller 140 may be disposed along flow lumen 130 to control flow. Control of flow, according to embodiments, may be an on/off type device, such as a clamp, whereby when flow controller is open flow is effected and when flow controller 140 is closed, flow is prevented. Flow controller 140 may also comprise, according to embodiments, a flow restrictor to ensure constant or predictable flow. According to embodiments, flow controller 140 may comprise a plurality of flow restrictors, clamps. According to other embodiments, flow controller may comprise an active pump.

Fill device 150 is disposed along flow lumen 130 and facilitates the filling of second chamber 120 with flow material. Fill device 150 may comprise a one-way valve, according to embodiments, whereby flow material is flowed through valve and into second chamber 120. Fill device 150 is a luer actuated port, according to embodiments. According to optional embodiments, fill valve comprises a device for putting a prefilled second chamber 120, such as a typical intravenous bag, into first chamber 110 after which first chamber 110 is pressurized.

Figure 2:
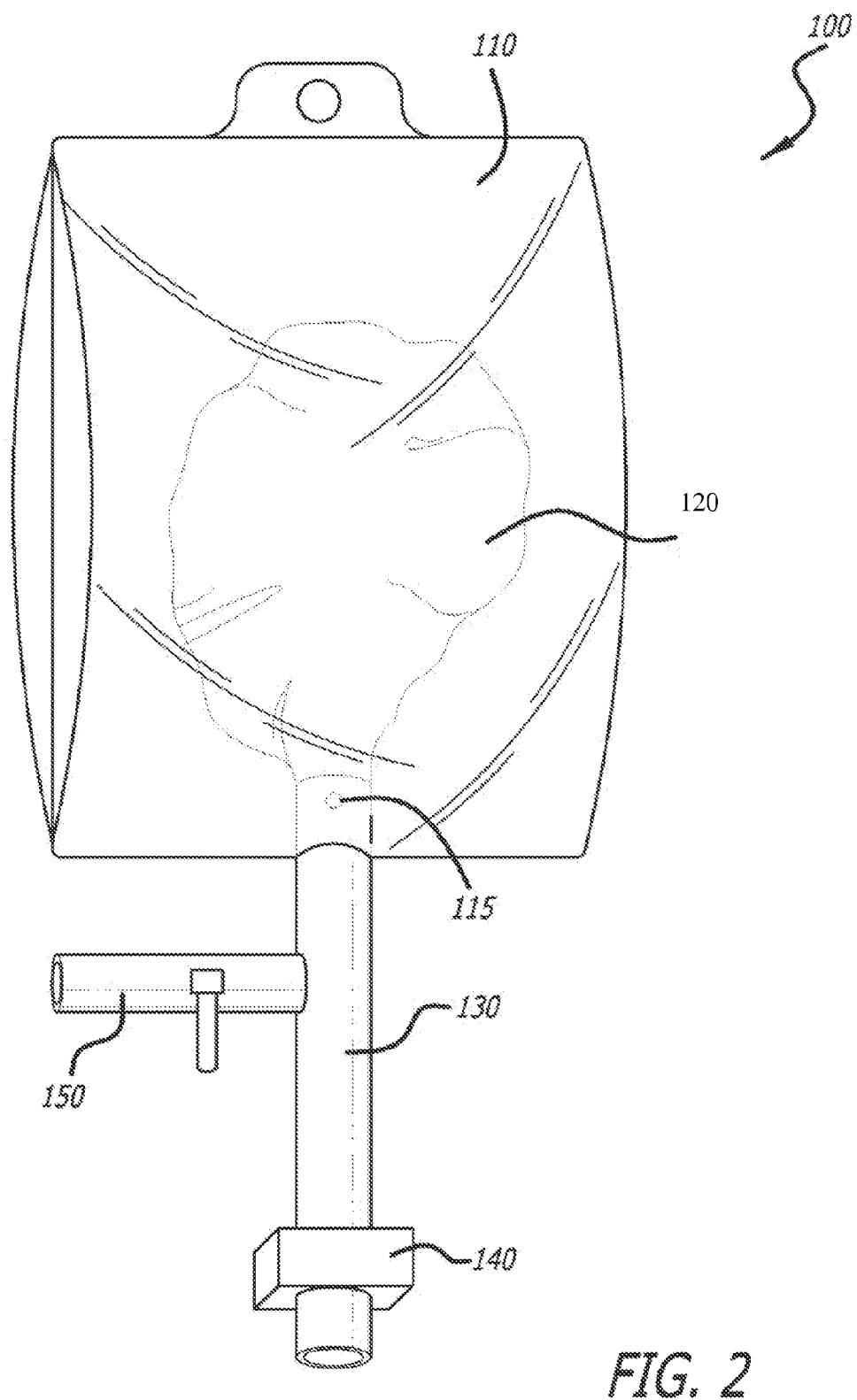
FIG. 2 is a cross sectional view of an embodiment of the pumps of the present disclosure, where the outer casing of the pump is a collapsible bag.

According to embodiments, and as shown in FIG. 1, first chamber 110 is a chamber that is able to be pressurized. According to embodiments, first chamber 110 may be made from any suitable rigid material, for example polycarbonate, ABS, or polyethylene. According to different embodiments, first chamber 110 may be made from flexible materials, for example PVC, polyethylene, silicon, polyurethane, or various rubbers. According to embodiments, first chamber 110 is sealed to prevent leakage of gas contained therein. According to embodiments, first chamber 110 may have a valve for repressurization or adjustment of pressure, as desired. According to embodiment and as illustrated in FIG. 2, first chamber 110 comprises a bag-like or collapsible device.

Sensor 115 is disposed in first chamber 110 to determine the volume of second chamber at predetermined intervals or in real time, as well as initial readings. The data collected from sensor will be used to measure flow material dispensed, as well as used to determine flow rate.

According to embodiments, and as well known and understood by artisans, methods for determination of the volume are expressly contemplated in the instant application. Pressure sensors may be used, as disclosed herein. According to embodiments, acoustic sensors, including a loud speaker and one or more microphones may be used to accurately determine the volume of first chamber 110 or second chamber 120, thereby allowing for calculation of the volume of flow material in the chambers. Acoustic volume determination technology is disclosed in U.S. Pat. Nos. 5,575,310 and 5,755,683, which are incorporated by reference; and U.S. Provisional Application Ser. No. 60/789,243, which is incorporated by reference. U.S. Pat Application Publication No. 2007/0219496, which is incorporated by reference, discloses still further methods for the determination of the volume of first chamber 110 or second chamber 120, including via optical, capacitive, deflection measure methods (detecting deflection of a membrane as pressure changes), thermal time of flight methods, or other methods for measuring the volume of a chamber. Each of these may be used instead of or in addition to pressure sensors.

Optionally, multiple sensors may be disposed in first chamber 110. For example, where Boyle's law is used to measure volume, a temperature sensor may be disposed in first chamber 110 along with a pressure sensor to improve accuracy of flow measurement. A plurality of the same sensors may be disposed into first chamber 110 in to more accurately determine the volume of second chamber 120.

Second chamber 120, according to embodiments, comprises a collapsible chamber that holds a flow material without appreciable leakage. When flow controller is in a state whereby flow is effected, flow from second chamber 120 is effected by the pressure differential across flow controller 140. Second chamber 120 may be made from PVC, polyisoprene, silicon, polyurethane, or other flexible materials.

According to embodiments, first chamber 110 comprises a rigid-walled chamber, as illustrated in FIG. 1. According to other embodiments, first chamber 110 comprises collapsible/movable wall(s), as illustrated in FIG. 2. According to embodiments, the collapsible/movable wall(s) illustrated in FIG. 2 comprises an elastomeric material, wherein the volume of first chamber 110 is predictably variable. To be predictably variable, for example, the modulus of elasticity is known, which provides a known total volume of first chamber as a function of pressure. According to other embodiments, the collapsible or movable wall comprises a non-stretchable material, whereby the volume of first chamber 110 is unaffected by changes in the pressure of first chamber 110.

Figure 3:
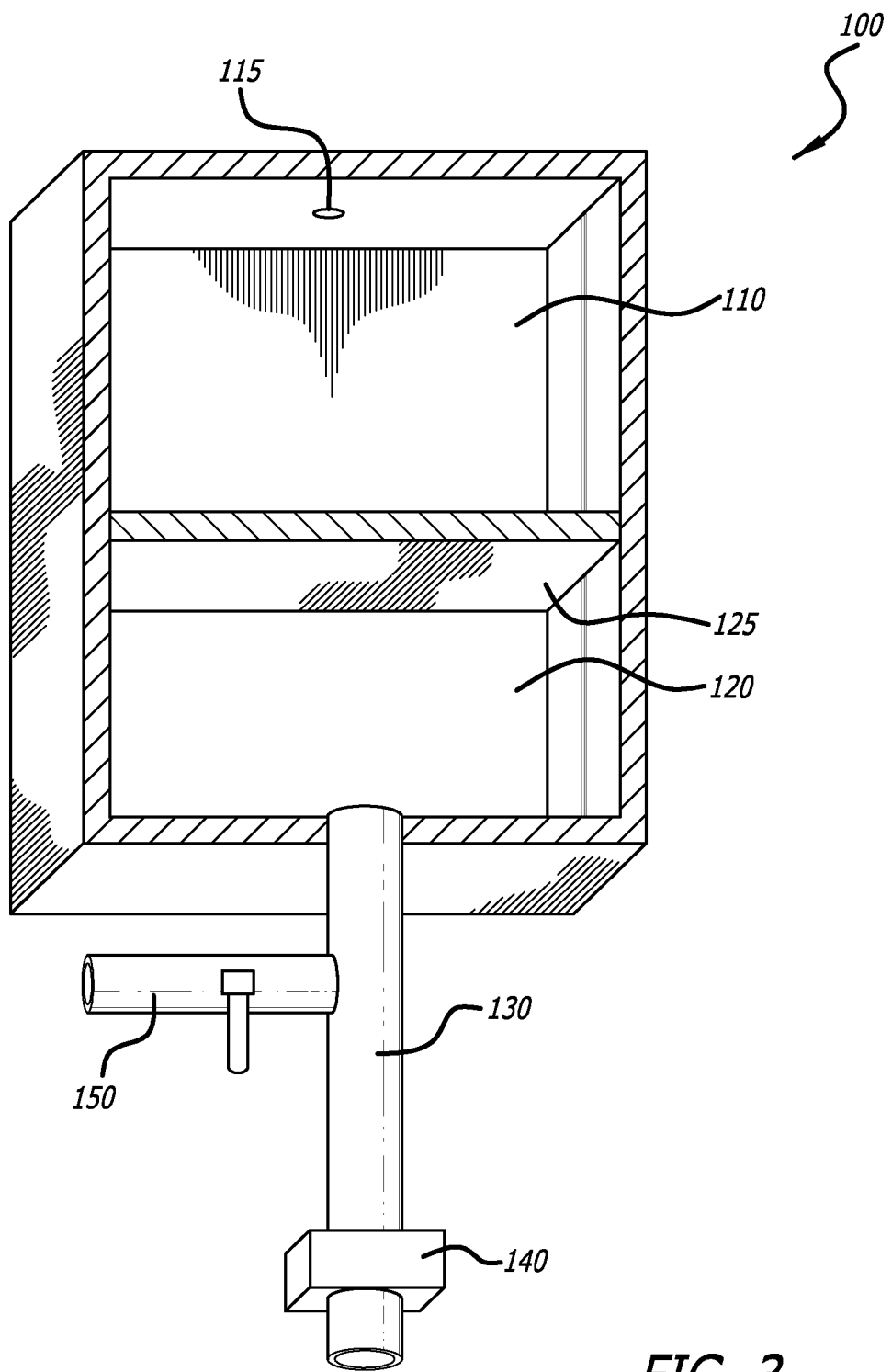
FIG. 3 is a cross sectional view of an embodiment of the pumps of the present disclosure.

According to embodiments and as shown in FIG. 3, second chamber 120 may be defined by a collapsible or movable diaphragm 125. Rather than collapsing second chamber 120, the movable or collapsible diaphragm 125 is moved whereby flow is effected.

For the purposes of the present application, second chamber 120 has three discrete states: empty, filled, and flowing. The empty state defines second chamber 120 when the volume is zero or a known empty volume. The filled state defines the second chamber 120 when it is filled with flow material. The flowing state defines a plurality of volumes where $$V_{2filled} > V_{2flowing} > V_{2empty}. \quad (1)$$

Typically, $V_{2flowing}$ is representative of the state wherein flow material is being dispensed from pump 100, for example. However, $V_{2flowing}$ may also be used for calculations during the filling of second chamber 120 with flow material.

Calculation of flow rate is based on the ideal gas law, that is:

$$PV = nRT. \quad (2)$$

The total volume of pump 100 is known, that is, the volume of first chamber 110 ($V_1$) plus the volume of second chamber 120 ($V_2$) is a constant, as shown:

$$V_1 + V_2 = c. \quad (3)$$

Thus, as flow material moves from $V_2$ to a delivery target, such as a patient, the volume of $V_1$ increases proportionally. Consequently, if $V_1$ is determined in a filled state and $V_1$ is determined in a flowing state at a time interval after flow material begins to flow from second chamber 120, the change in volume of $V_1$ over the time interval t is the flow rate over that time interval.

$$\text{flowrate} = \frac{\Delta V_2}{\Delta t} \quad (4)$$

where $\Delta t$ is the time interval over which $\Delta V_1$ and $\Delta V_2$ are measured.

However, the volume of second chamber ($V_2$) is not measured directly. Rather, changes in $V_2$ are measured indirectly from the changing volume of $V_1$. Measurements of the volume of $V_1$ are accomplished with data collected from the sensors.

Turning again to the ideal gas law, because first chamber 110 is sealed, the number of molecules (n) of gas in first chamber 110 remains constant. Additionally, R is constant. Therefore, $$nR = k \quad (5)$$

where k is a constant. Thus, $$PV = kT \tag{6}$$

$$\frac{PV}{T} = k. \tag{7}$$

Because first chamber 110 is sealed, k remains constant. Additionally, pressure sensor and optional temperature sensor disposed in first chamber 110 allows for measurement of $P_{1filled}$, $P_{1flowing}$, $T_{1filled}$, and $T_{1flowing}$, which provides data sufficient for calculation of $V_{2filled}$. Using $V_{1filled}$, $V_{1flowing}$ can be calculated:

$$\frac{P_{1filled} V_{1filled}}{T_{1filled}} = \frac{P_{1flowing} V_{1flowing}}{T_{1flowing}}. \tag{8}$$

Artisans will understand the filled state comprises the end state at each discrete time interval in which flow rate is measured. Indeed, according to embodiments, the filled state of the prior time interval may comprise the filled of the succeeding time interval, and so forth:

$$\frac{P_{1flowing}^{\Delta t=0} V_{1flowing}^{\Delta t=0}}{T_{1flowing}^{\Delta t=0}} = \frac{P_{1flowing}^{\Delta t=x} V_{1flowing}^{\Delta t=x}}{T_{1flowing}^{\Delta t=x}} \tag{9}$$

where $\Delta t$ is the elapsed time. According to embodiments, when $\Delta t=0$, the flowing state is equal to the filled state. According to other embodiments, when $\Delta t=0$, flow material has already been dispensed from second chamber 120 and $\Delta t$ is set to zero (or the current value of $\Delta t$ is treated as if it is zero) to determine a flow rate from that point forward. When $\Delta t \geq 1$, flow material has been dispensed from second chamber 120. Artisans will readily appreciate that each time interval represented by $\Delta t$ may represent the aggregate time since the flow of flow material for second chamber 120 began, according to embodiments. According to other embodiments, $\Delta t$ may represent a snapshot from a known state of second chamber 120 to an unknown state after flow material has been dispensed.

To more clearly illustrate the principle of determining $\Delta V_1$, temperature will be assumed to be constant for the purposes of the next set of equations. Thus, $$P_{1filled} V_{1filled} = P_{1flowing} V_{1flowing}. \tag{10}$$

Therefore, solving for $V_{flowing}$ of first chamber 110 yields $$V_{1flowing} = \frac{P_{1filled} V_{1filled}}{P_{1flowing}}. \tag{11}$$

However, $V_{1filled}$ is unknown and must be calculated from the total volume of pump c and from knowing the filled volume ($V_{2filled}$) of flow material put into second chamber 120:

$$V_{1filled} = c - V_{2filled} \tag{12}$$

Thus, the total amount of volume flowed may be calculated using the equation, based on the proportionality of flow between first chamber 110 and second chamber 120:

$$\text{flowrate} = \frac{V_{2flowing} - V_{2filled}}{\Delta t} \tag{13}$$

Thus, to determine $V_{1flowing}$, we can use the relationship expressed in equation (11). As $V_{1filled}$ is unknown, substituting known values of c and $V_{2filled}$, the following equation results:

$$V_{1flowing} = \frac{P_{1filled}(c - V_{2filled})}{P_{1flowing}}. \tag{14}$$

Flowrate may be calculated as:

$$\text{flowrate} = \frac{\frac{P_{1filled}(c - V_{2filled})}{P_{1flowing}} - V_{1filled}}{\Delta t}. \tag{15}$$

Adding temperature back to the equation allows for a more precise measurement of flow rate and is easily accomplished:

$$\text{flowrate} = \frac{\frac{P_{1filled}(c - V_{2filled})}{P_{1flowing}} - V_{1filled}}{\Delta t} \left( \frac{T_{1flowing}}{T_{1filled}} \right). \tag{16}$$

According to embodiments, measurements of flow rate are taken at discrete time intervals. These time intervals may range from many measurements per fraction of seconds to measurements taken over the course of minutes, hours, or days, depending on the specific application. Accordingly, measuring flow rate provides about real-time feedback, which may be used to adjust flow rate via flow controllers, such as flow restrictors, flow metering devices, valves, or with mechanical devices used conjunction with second chamber 120. By coupling the measurement of flowrate to flow controllers, flow may be closely regulated by modulating the flow controllers in response to the measured flowrate. For example, if flow controller 140 comprises a clamp, then feedback system may open the clamp when additional flow of flow material is needed and close the clamp when too much flow has occurred. Thus, the combination of a flow controller and the about real-time flow measurement provides a platform to deliver measurably accurate volumes of a flow material.

According to embodiments, to dispense flow material from pump 100, a calibration step is necessary. The calibration step determines the volume of second chamber 120 prior to filling with a flow material ($V_{2empty}$), which is necessary to determine flow rate, as described below using the ideal gas law or Boyle's law.

According to embodiments, the simplest method for the determination of $V_{2empty}$, is to know the volume of flow material put into second chamber 120. This is accomplished by injecting a known amount of flow material into second chamber 120 via fill device 150 or using a disposable second chamber 120 (i.e., an IV bag) holding a known volume.

According to embodiments, calibration may also be accomplished by calculating, using the ideal gas law, the volume of second chamber 120 from a known starting volume in an empty state. If second chamber 120 occupies a known empty volume, for example using the pump of FIG. 3, wherein the diaphragm rests at a set position when second chamber 120 is empty, for example 0 ml or 10 ml, then prior to filling of second chamber 120 with a flow material, the pressure and temperature of first chamber are measured. The initial volume of second chamber 120 is then calculated after flow material is put into second chamber 120 using an equation to measure flow rate, which is derived in detail below:

$$V_{1filled} = \frac{P_{1empty}T_{1empty}T_{1filled}}{T_{1empty}P_{1filled}} \quad (17)$$

$$V_{2filled} = c - V_{1filled} \quad (18)$$

where $V_{2filled}$ is the volume of second chamber 120 after it is filled with a flow material; $V_{1filled}$ is the volume of the first chamber 110 when second chamber is filled; c is the fixed volume of pump 100; $P_{1empty}$, $T_{1empty}$, and $V_{1empty}$ are the pressure, temperature, and volume respectively of first chamber 110 prior to filling second chamber 120; and $P_{1filled}$, $T_{1filled}$, and $V_{1filled}$ are the pressure, temperature, and volume of first chamber 110 after filling second chamber 120 with a flow material. According to embodiments, flow is effected because the pressure of first chamber 110 and the pressure in second chamber 120 exceed the pressure at the point of delivery of the flow material. Accordingly, flow rate may be calculated with high precision and in about real time. Prior to determination of flow rate, the filled state of pump 100 must be measured, according to equation (17), substituting empty values with filled values.

According to embodiments, first chamber 110 may be made from expandable materials. In such embodiments, first chamber 110 may be a disposable bag or similar flexible-type container such as an IV-type bag, for example as shown in FIG. 2, which expands or contracts depending on the pressure within the first chamber. Thus, the above equations must account for the effects expansion or contraction due to change of pressure within first chamber 110. In other words, as pressure increases, the volume within first chamber 110 will change in a predictable way and visa versa. For example, by including in the calculations a factor incorporating the modulus of elasticity of the material from which first chamber 110 is made into the $V_1$, the change in the volume of first chamber 110 is reasonably predictable, for example when using embodiments similar to that illustrated in FIG. 2.

Accuracy of the determination of the change in $V_1$ attributable to the elasticity of the material from which first chamber is made is improved by calibrating the system at a known initial pressure of first chamber 110 and volume of second chamber 120. Accordingly, first chamber 110 would be designed to have a known volume in this initial state. As pressure increases, the calculated additional volume due to expansion of first chamber 110 may be added to the initial volume to derive an accurate value of $V_1$.

Referring again to the calibration step, as the volume of second chamber 120 increases during filling with the flow material, the volume of first chamber 110 is decreased and the pressure within first chamber 110 increases. At the same time, if first chamber 110 is made from non-rigid materials there will be predictable expansion of the dimensions of first chamber 110, with increased resulting volume. Thus, to determine the actual volume of first chamber 110 after the initial state, the pressure of first chamber is measured and volume is calculated as described previously, taking into account the incremental volume increase or decrease of first chamber 110 observed due to elasticity of material from which first chamber 110 is made.

According to alternative-type embodiments, a method for accounting for the change in $V_1$ due to expansion or contraction of the material from which first chamber 110 is made is accomplished by use of values from a lookup table that approximates change in volume of first chamber 110 as a function of pressure within first chamber 110. The lookup table, according to embodiments, is based upon averaged value for a plurality of the same first chamber 110 having the same dimensional parameters and will provide a reasonably approximate factor to add or subtract to $V_1$ at a plurality of given measured pressures.

These principles are illustrated in the following equations. Let $V_1^E$ be the supplemental volume of first chamber as first chamber 110 expands or contracts. In systems where first chamber 110 is made from rigid materials, the volume of first chamber 110 plus the volume of second chamber 120 is constant, as expressed in equation (3).

In system where first chamber 110 is made from expandable materials, however, a factor must be added to c denoting the added or lost volume occurring due to expansion or contraction of the first chamber 110.

$$V_1 + V_2 = c + V_1^E \quad (19)$$

Thus, the volume of $V_1$ may be calculated as:

$$V_1 = c + V_1^E - V_2. \quad (20)$$

Thus, in systems where first chamber 110 is made from expandable materials, equation (16) is modified to account for the expanded first chamber 110:

$$\text{flowrate} = \frac{\frac{P_{1filled}(c + V_1^E - V_{2filled})}{P_{1flowing}} - V_{1filled}}{\Delta t} \left(\frac{T_{1flowing}}{T_{1filled}}\right). \quad (21)$$

Artisans will readily recognize that $V_1^E$ may be calculated if the modulus of elasticity is known or may be simply recorded as a set of values within a table for quick lookup, especially in situations where a microprocessor is not designed to perform series of complex calculations or where power consumption is an issue.

While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A device comprising:
a pressurizable, fluid-tight, sealed first chamber, the first chamber comprising a flexible material that is expandable and collapsible depending on a pressure of a pressurized substance within the first chamber to define a variable volume of the first chamber;
a second chamber fully enclosed within the pressurized substance of the first chamber for holding a flow material;
at least one flow lumen in flow material communication with the second chamber;
at least one sensor disposed in the first chamber;
a flow controller disposed along the flow lumen; and a microprocessor for calculating flow rate from data provided by the at least one sensor, the flow rate calculation accounting for the variable volume of the first chamber;

wherein the first chamber is configured such that when the pressurized substance having a pressure higher than the flow material in the second chamber is in the first chamber, the pressurized substance effects a change of volume of the second chamber; and wherein the microprocessor controls the flow controller.

2. The device of claim 1, further comprising a fill port for filling the second chamber with the flow material.

3. The device of claim 1, wherein the sensor is a pressure sensor.

4. The device of claim 3, further comprising at least one temperature sensor disposed in the first chamber.

5. The device of claim 1, wherein the flow controller is a flow restrictor.

6. The device of claim 1, wherein the flow controller is a flow metering device.

7. The device of claim 1, wherein an expansion of the flexible material is a function of the pressure of the first chamber.

8. A device comprising:

a pressurizable first chamber, the first chamber comprising a flexible material that is expandable and collapsible depending on a pressure within the first chamber;

a second chamber enclosed by the first chamber for holding a flow material;

at least one flow lumen in flow material communication with the second chamber;

at least one sensor disposed in the first chamber;

a flow controller disposed along the flow lumen; and a microprocessor for calculating flow rate from data provided by the at least one sensor, the flow rate calculation accounting for expansion and contraction of the first chamber due to changes in pressure within the first chamber, wherein the first chamber is configured to be filled with a pressurized substance that directly contacts an inner perimeter of the first chamber and that contacts an outer perimeter of the second chamber and that effects a change of volume of the second chamber; and wherein the microprocessor controls the flow controller.

9. The device of claim 8, further comprising a fill port for filling the second chamber with the flow material.

10. The device of claim 8, wherein the sensor is a pressure sensor.

11. The device of claim 10, further comprising at least one temperature sensor disposed in the first chamber.

12. The device of claim 8, wherein the flow controller is a flow restrictor.

13. The device of claim 8, further comprising at least one temperature sensor wherein the microprocessor gathers data from the temperature sensor to compute a flow rate of flow material transferred through the flow lumen from the second chamber.

14. A method comprising:

providing a pump including:

(a) a pressurizable, fluid-tight, sealed first chamber, the first chamber comprising a flexible material that is expandable and collapsible depending on a pressure of a pressurized substance within the first chamber with a volume of the first chamber being predictably variable as the first chamber expands and collapses;

(b) a second chamber fully enclosed within the pressurized substance of the first chamber for holding a flow material;

(c) at least one sensor disposed in the first chamber and a microprocessor adapted to calculate flow rate of the flow material from data provided by the sensor based at least in part on the predictably variable volume of the first chamber;

(d) a flow lumen in flow material communication with the second chamber; and (e) a flow controller; and causing the flow material to flow from the second chamber and through the flow controller with the pressurized substance in the first chamber having a pressure greater than the flow material in the second chamber thereby changing a volume of the second chamber.

15. The method of claim 14, wherein providing the pump includes providing a pump wherein the sensor is a pressure sensor.

16. The method of claim 15, wherein providing the pump comprises providing a pump wherein at least one temperature sensor is disposed in the first chamber.

17. The method of claim 15, wherein providing the pump includes providing a pump wherein the flow controller is a flow restrictor.

18. The method of claim 14, wherein providing the pump includes providing a pump wherein the flow controller is a flow metering device.

19. The method of claim 15, further comprising computing flow rate from the data provided by the pressure sensor with the microprocessor and controlling the flow controller with the microprocessor.

20. The method of claim 14, further comprising pressurizing the first chamber prior to filling the second chamber with the flow material.

21. The device of claim 1, wherein the microprocessor is configured to determine the flow rate according to an equation:

$$\text{flowrate} = \frac{\frac{P_{1filled}(c + V_1^E - V_{2filled})}{P_{1flowing}} - V_{1filled}}{\Delta t}\left(\frac{T_{1flowing}}{T_{1filled}}\right)$$

wherein $P_{1filled}$ and $T_{1filled}$ are the pressure and temperature, respectively, in the first chamber when the second chamber is full with flow material, $V_{1filled}$ and $V_{2filled}$ are the volumes of the first chamber and second chamber, respectively, when the second chamber is full with flow material, $P_{1flowing}$ and $T_{1flowing}$ are the pressure and temperature, respectively, of the first chamber when flow material is flowing from the second chamber, $\Delta t$ is a time interval between which $P_{1filled}$ and $P_{1flowing}$ are measured and $V_1^E$ is a supplemental volume of the first chamber as the first chamber expands or contracts.

* * * * *